US00RE34757E

United States Patent [19]

Smith et al.

[11] E Patent Number: Re. 34,757

[45] Reissued Date of Patent: Oct. 18, 1994

[54] COMBINED ELECTROPHORESIS-ELECTROSPRAY INTERFACE AND METHOD

[75] Inventors: Richard D. Smith; Harold R. Udseth, both of Richland, Wash.; José A. Olivares, Los Alamos, N. Mex.

[73] Assignee: Battelle Memorial Institute, Richland, Wash.

[21] Appl. No.: 803,145

[22] Filed: Dec. 4, 1991

Related U.S. Patent Documents

Reissue of:

[64] Patent No.: 4,885,076
Issued: Dec. 5, 1989
Appl. No.: 178,046
Filed: Apr. 5, 1988

[51] Int. Cl.[5] ..... G01N 27/26; G01N 27/447; H01J 49/02; H01J 27/02

[52] U.S. Cl. ..... 204/299 R; 204/180.1; 250/288; 250/423 R

[58] Field of Search ..... 250/423 R, 288 A, 288, 250/424; 204/299 R, 180.1

[56] References Cited

U.S. PATENT DOCUMENTS

| | | | |
|---|---|---|---|
| 4,160,161 | 7/1979 | Horton | 250/281 |
| 4,209,696 | 6/1980 | Fite | 250/281 |
| 4,570,068 | 2/1986 | Sakairi et al. | 250/288 |
| 4,667,100 | 5/1987 | Lagna | 250/282 |
| 4,705,616 | 11/1987 | Andresen | 204/299 R |
| 4,977,785 | 12/1990 | Willoughby et al. | 250/288 X |

FOREIGN PATENT DOCUMENTS 84302751.7 4/1984 European Pat. Off. .

OTHER PUBLICATIONS

"Capillary Zone Electrophoresis", J. W. Jorgenson, et al., Science, vol. 222, pp. 266–272, Oct. 1983.

Smith et al, (Smith), Ser. No. 07/034875, Filed Apr. 6, 1987.

Whitehouse et al, "Electrospray Interface for Liquid Chromatographs and Mass Spectrometers", *Analytical Chemistry,* vol. 57, No. 3 (Mar. 1985), pp. 675–679.

"Electrospray Interface for Liquid Chromatographs and Mass Spectrometers", C. M. Whitehouse, et al., Anal. Chem., pp. 675–679.

"Microcolumn High Performance Liquid Chromatography", P. Kurcera, ed., The Journal of Chromatography Library, vol. 28, Amsterdam, 1984.

"Detectors for Use with Small Bore Columns", Small Bore Liquid Chromatography Columns: Their Properties & Uses, Raymond P. W. Scott, ed., vol. 72, John Wiley & Sons, New York, 1984.

"Mixed Zone Analysis in Isotachophoresis with Selective Detection by Mass Spectrometry Applied to the (List continued on next page.)

*Primary Examiner*—John Niebling
*Assistant Examiner*—John S. Starsiak, Jr.
*Attorney, Agent, or Firm*—Marger, Johnson, McCollom & Stolowitz

[57] ABSTRACT

A system and method for analyzing molecular constituents of a composition sample includes: forming a solution of the sample, separating the solution by capillary electrophoresis into an eluent of constituents longitudinally separated according to their relative electrophoretic mobilities, electrospraying the eluent to form a charged spray in which the molecular constituents have a temporal distribution; and detecting or collecting the separated constituents in accordance with the temporal distribution in the spray. A first high-voltage (e.g., 5-100 KVDC) is applied to the solution. The spray is charged by applying a second high voltage (e.g., ±2-8 KVDC) between the eluent at the capillary exit and a cathode spaced in front of the exit. A complete electrical circuit is formed by a conductor which directly contacts the eluent at the capillary exit, or by conduction through a sheath electrode discharged in an annular sheath flow about the capillary exit.

54 Claims, 15 Drawing Sheets

OTHER PUBLICATIONS

Quantitation of Hydrogenation Products of Aromatic Quaternary Ammonium Compounds", Anal. Chem., pp. 391–396, 1985.

"Negative Ion Production with the Electrospray Ion Source", M. Yamashita & J. B. Fenn, The Journal of Physical Chemistry, vol. 88, No. 20, 1984, pp. 4671–4675.

"Electrospray Mass Spectroscopy of Macromolecule Degradation in the Electrospray", D. Teer & M. Dole, The Journal of Polymer Science: Polymer Physics Edition, vol. 13, pp. 985–995, 1975.

"Electrospray Mass Spectroscopy of Macromolecules: Application of an Ion Drift Spectrometer", J. Gieniec, et al., p. 10.

"Electrospray Ion Source, Another Variation on the Free-Jet Theme", M. Yamashita & J. B. Fenn, The Journal of Physical Chemistry, pp. 4451–4459, 1984.

Low Pressure Syringe Pump
Pump
H.V.2
±HV2

FIG. 14A
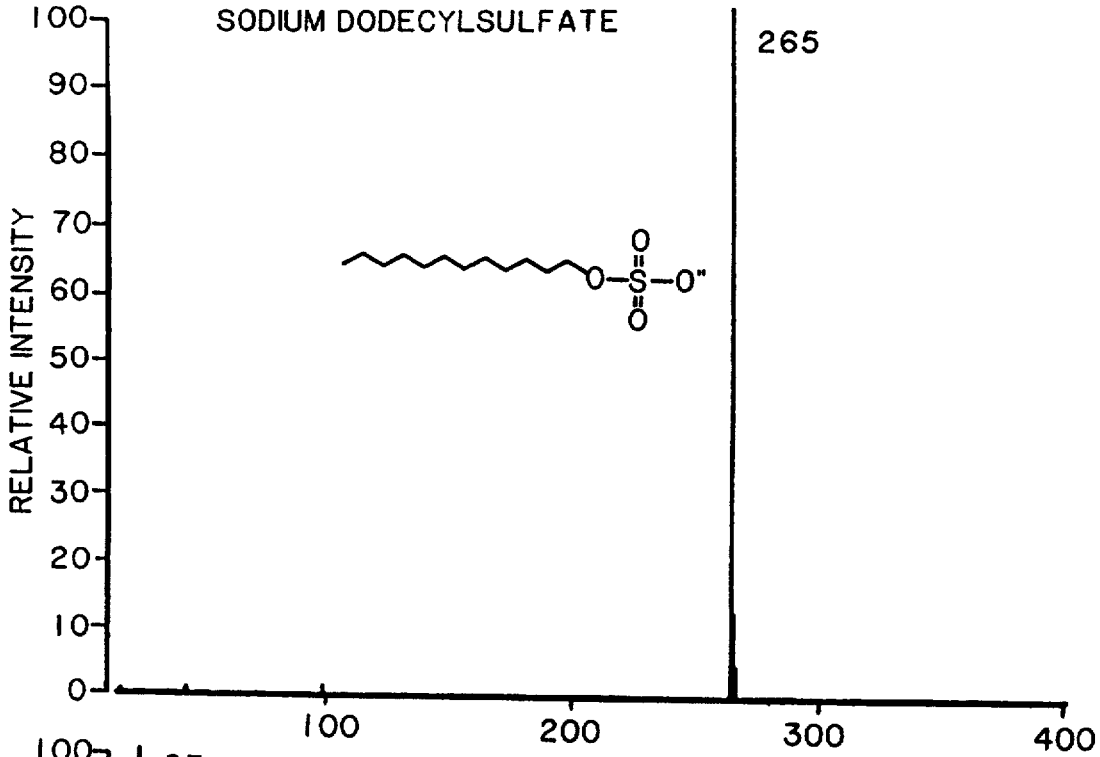
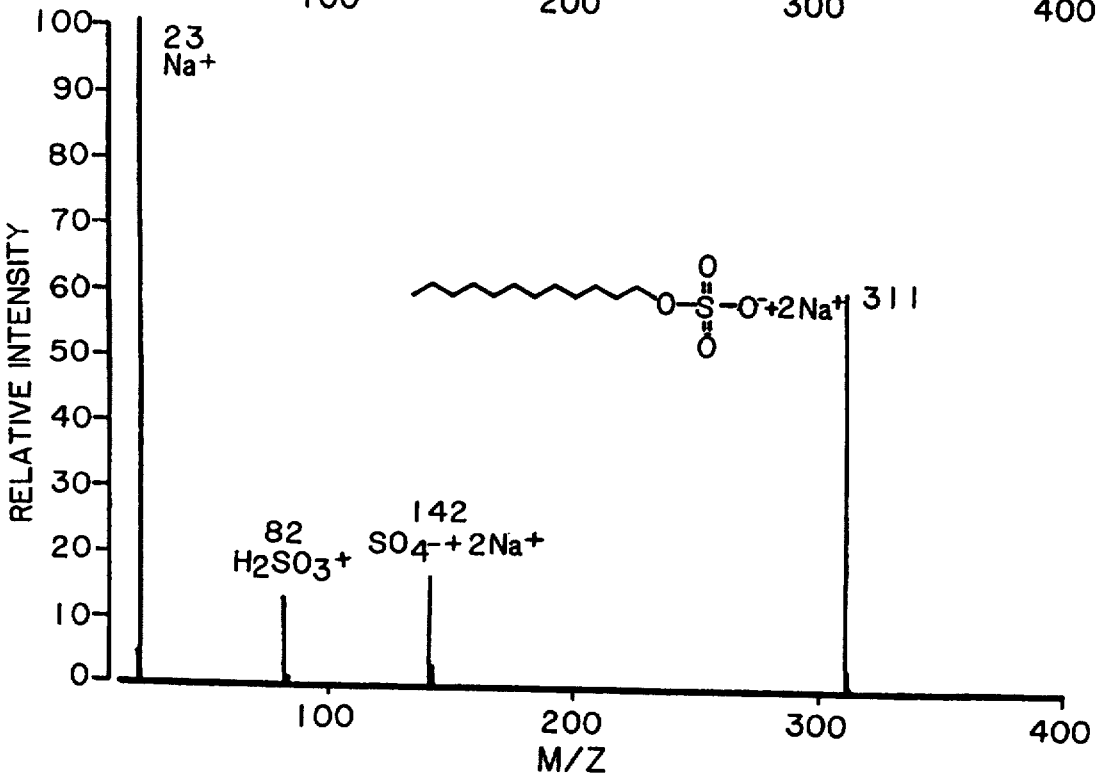
FIG. 14B

COMBINED ELECTROPHORESIS-ELECTROSPRAY INTERFACE AND METHOD

Matter enclosed in heavy brackets [ ] appears in the original patent but forms no part of this reissue specification; matter printed in italics indicates the additions made by reissue.

The United States Government has rights in this invention in accordance with the operating contract DE-AC-06-76RLO 1830 between Battelle Memorial Institute and the U.S. Department of Energy. RELATED APPLICATION DATA This application is related to copending, commonly-assigned U.S. patent application Ser. No. 07/034,875, filed Apr. 6, 1987, by R. D. Smith and J. Olivares entitled, "Combined Electrophoretic-Separation and Electrospray Method and System."

BACKGROUND OF THE INVENTION

This invention relates to a method and apparatus for analyzing chemical compositions and more particularly to a method and system for combining free zone electrophoretic separation of a mixture sample with electrospraying to interface with on-line detection or off-line collection apparatus. The invention finds especially advantageous application in combining capillary zone electrophoresis and mass spectrometry (CZE-MS).

Numerous systems employed in the separation and analysis of analytes are known in the prior art. However, these prior art systems are not necessarily broadly applicable to the separation and/or analysis of analytes which comprise complex materials, or high molecular weight, nonvolatile, and highly polar compounds.

One known method for separation of analyte mixtures, free zone electrophoresis in small diameter capillaries or capillary zone electrophoresis (CZE), is used for a wide variety of analyses including high resolution separations of amino acids, peptides, proteins and complex salt mixtures. CZE employs a capillary with an electric field gradient to separate the analyte constituents, particularly ions, by difference in electrophoretic mobilities in addition to electroosmotic flow in the capillary. The electroosmotic flow results when an electrical double layer of ions forms at the capillary surface and an electrical field is imposed lengthwise along the capillary. The field causes the ions to migrate towards the oppositely charged electrode at rates determined by the electrophoretic mobility of each analyte. In the resulting bulk electroosmotic flow, positively charged ions, neutral species, and negatively charged ions elute at different time intervals. The extent and speed of this separation are determined by differences in the electrophoretic mobilities of the analytes, the length of the capillary, the bulk electroosmotic flow and by the strength of electric field.

FIG. 1 is a schematic illustration of the customary arrangement of a CZE system. In this arrangement, a complete high voltage electrical circuit must be formed between opposite ends of a fused silica capillary A filled with a buffer solution and extending through a flourescence detector B. This is accomplished by immersing both ends of the capillary in beakers C, D of the buffered solutions at each end of the system.

CZE detection is currently limited to analysis by ultraviolet or fluorescent detection techniques, so as not to degrade the quality of the separation. Such detection techniques have been adequate for species that fluoresce, absorb, or are amenable to derivatization with fluorescing or absorbing chromophores. These detectors also impose cell volume and sample size limitations that preclude high separation efficiencies concurrent with high sensitivities. Structural information necessary for the correct identification of unknown analytes and their constituents cannot be obtained using these detectors due to the small sample volume and the limited spectroscopic data inherent in UV and fluorescence detection techniques. These limitations constitute a major drawback in the use of CZE for the separation and identification of complex mixtures since many compounds cannot be detected, and, if detectable, cannot be unambiguously identified. A detailed discussion of CZE can be found in an article by Jorgenson, et al., in the publication "Science" (1983), Vol. 222, beginning at page 266.

A well-known analytical technique which combines a separation technique with an analytical detection device is gas chromatography-mass spectrometry (GC-MS). In this method, GC can provide separations of sufficiently volatile compounds which are then ionized and analyzed by mass spectrometry. GC-MS has become established as the definitive analytical technique for amenable compounds, i.e., compounds having sufficient volatility for GC separation and ionization by conventional gas phase electron impact or chemical ionization methods used in mass spectrometry.

Such an established capability of broad application is not known to exist for nonvolatile compounds and mixtures. Systems for combining liquid chromatography with mass-spectroscopy are described in U.S. Pat. No. 4,209,696 and in European Patent Application No. 84302751.7, which are incorporated herein by reference. In these systems, carrier liquid from a liquid chromatograph is electrosprayed and then analyzed by mass spectrometry. To work, electrospray requires an ionic strength of less than about $10^{-2}$ molar. Various other attempts to combine liquid chromatography with mass spectroscopy are described in "Microcolumn High Performance Liquid Chromatography," P. Kucera, Ed., J. Chromatography Library, Vol. 28, Chap. 8, pp. 260–300 (1984) and in "Small Bore Liquid Chromatography Columns: Their Properties and Uses," R. P. W. Scott, ed., Vol. 72, pp. 104–114 (1984). Unfortunately, these systems and ther LC-MS approaches suffer significant limitations due to their inability to effectively separate complex mixtures, their limited separation efficiency, and the time required for analysis or separation. Combined liquid chromatography-mass spectroscopy does not provide high resolution separations. In liquid chromatography, the maximum number of theoretical plates is limited to about 10,000 for reasonable separation times (under about one hour). In contrast, CZE has been shown to be able to provide over one million theoretical plates in the same time.

Accordingly, a need remains for a method of separation that has the high-resolution separation of efficiencies of CZE and, additionally, an ability to analyze a wide range of nonvolatile compounds.

SUMMARY OF THE INVENTION

This invention relates to a system and method for interfacing the free zone electrophoretic separation of a sample and electrospray, respectively, so that the molecular constituents of the electrosprayed eluent produced have a temporal distribution and can be concentrated by evaporation of the solvent. The electrosprayed eluent can be subsequently analytically detected on-line using mass spectrometry, or other analysis methods, or can be collected off-line for analysis or other applications requiring highly-purified samples.

A system and method for analyzing molecular constituents of a sample includes: forming a solution of the sample, separating the solution by capillary electrophoresis into an eluent of constituents longitudinally separated according to their relative electrophoretic mobilities, electrospraying the eluent to form a charged spray in which the molecular constituents have a temporal distribution; and detecting or collecting the separated constituents in accordance with the temporal distribution in the spray.

A first high-voltage (e.g., 5–100 KVDC) is initially applied to the solution to separate its constituents. The separated eluent is electrosprayed and the spray is charged by applying a second high voltage (e.g., +/−2–8 KVDC) between the eluent at the capillary exit and a counter electrode spaced in front of the exit. A complete electrical circuit is formed by a conductor which directly contacts the eluent at the capillary exit.

Capillary electrophoresis includes variations such as electrokinetic chromatography or isotachophoresis. Electrospraying includes processes which involve electric fields, and may include concurrent utilization of nebulizing gases or heating methods.

The sample can include complex, high-molecular-weight, nonvolatile and highly-polar compounds. Ordinarily, the solution includes a buffering agent. Detection can be by apparatus that does not depend on UV or fluorescence of the constituents and that is capable of identifying and quantifying, or providing universal detection of, the constituents.

The interface includes means for applying a first high voltage potential between the source of sample solution and the capillary outlet, to effect electrophoretic separation in the sample, and means for applying a second high voltage potential between the capillary outlet and the collector or detector, to electrospray and ionize the separated sample as it is discharged. In one embodiment, the capillary outlet end can be metallized to conductively couple the eluent to the second high voltage source. In a second embodiment, an annular sheath flow of a sheath flow liquid is discharged simultaneously around the sample flow from the capillary outlet. The latter interface permits greater and more uniform ion current, not limited by capillary flow rates and composition. It also simplifies interface design and fabrication, allows making electrical contact at the capillary end without gas generation problems, loss of separation efficiency due to dead space, and electrospray instability.

The invention finds particular advantage in interfacing capillary-zone electrophoresis and mass spectrometry (CZE-MS). In one embodiment of this application, the CZE cathode serves as an electrospray needle for spraying a separated sample into a mass-spectrometer. The analyte eluent at the capillary outlet is biased relative to the mass spectrometer at a voltage potential sufficient to produce the electrospray, which is then sampled by the mass spectrometer. Electrospraying is carried out at near-atmospheric pressure. Accordingly, the mass spectrometer preferably includes a differentially pumped input chamber. The interface can further include an ion lens to aid ion transmission into the detector. It can also include means for desolvating or vaporizing the ionized spray to form an ion vapor phase stream into the mass spectrometer.

The foregoing and other objects, features and advantages of the invention will become more readily apparent from the following detailed description which proceeds with reference to the drawings.

BRIEF DESCRIPTION OF THE DRAWINGS

FIG. 14 shows ESI mass spectra of aqueous solutions of sodium dodecylsulfate obtained in the negative (A) and positive (B) ion modes.

DETAILED DESCRIPTION OF A PREFERRED EMBODIMENT

Description of CZE-Electrospray Interface

Figure 2:
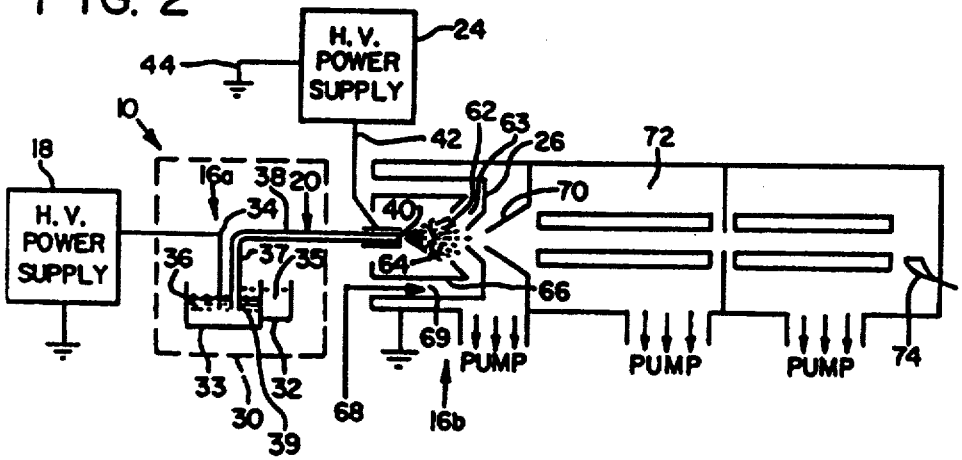
FIG. 2 is a schematic illustration of apparatus for capillary zone electrophoresis-mass spectrometry (CZE-MS) in accordance with the invention.
Figure 2A:
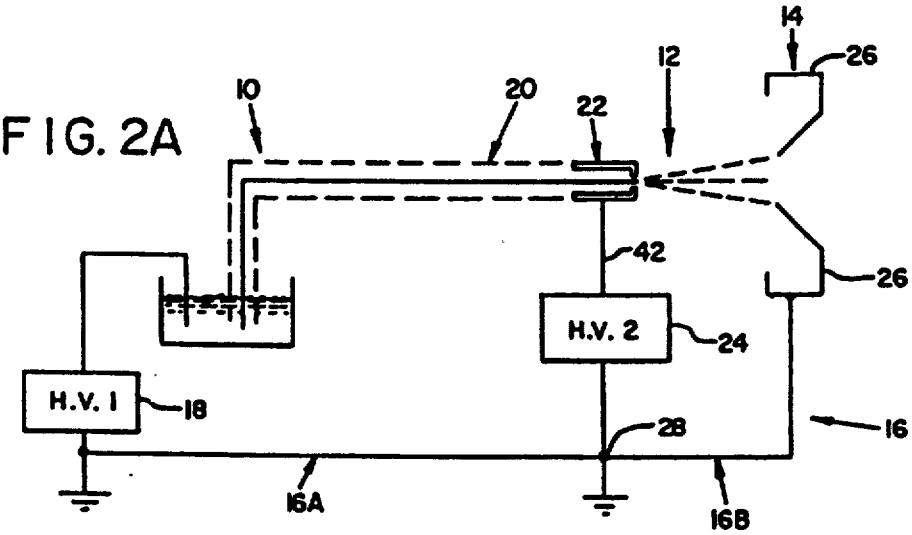
FIG. 2A is an electrical circuit diagram of the apparatus of FIG. 2.

FIG. 2 shows an apparatus for combined CZE-electrospray-mass spectrometer (CZE-MS) in accordance with a preferred embodiment of the present invention. FIG. 2A is an electrical circuit diagram of a generalization of the system of FIG. 2.

Referring first to FIG. 2A, a CZE-electrospray interface according to the invention generally comprises a capillary-zone electrophoresis (CZE) subsystem 10, an electrospray interface 12, a detection or collection device 14, and a high voltage electrical circuit 16. The CZE subsystem 10 and electrospray interface 12 form integral parts of the electrical circuit 16. Specifically, the CZE subsystem forms a part of a subcircuit 16A which includes a first high voltage supply 18 and capillary 20 having an outlet nozzle 22. The electrospray interface forms subcircuit 16B, which includes a second high voltage supply 24 and a counter-electrode 26 in the detector/collector 14. The two subcircuits are electrically interconnected at nozzle 22 and node 28, for example, ground. Optionally, a third power supply (not shown) can be used to bias the counterelectrode relative to node 28.

Referring next to FIG. 2, the CZE subsystem 10 includes an electrically insulated sampling box 30, provided to isolate the first high voltage system 16A from the outside environment. For example, a Lucite or Plexiglas box can be employed for this purpose. From a safety standpoint, this portion of the system is isolated because of the dangers to the user from this high voltage application.

Within box 30 are a sample injection reservoir 32 and a buffer reservoir 33 which contain the analyte sample and the CZE buffer solution in separate containers. High voltage system 16A includes a first high voltage power supply 18 and an electrode or microsampling arm 34 extending into the reservoir 33. An analyte sample solution 35 is formed in reservoir 32 by adding a suitable chemical solvent to a sample of the material to be analyzed. A buffering agent 36 is provided in reservoir 33. Typically, the reservoir to which either solution is added comprises a standard micro-beaker or other liquid container made of glass or the like.

A capillary 20 is also disposed within the sampling box 30. The capillary 20 may have a bend with a vertical inlet section 37 (depending upon sample introduction method) and horizontally-disposed outlet section 38, and includes respective inlet and outlet ends 39 and 40. The capillary inlet end 39 extends into sample solution reservoir 32 during injection of the sample solution 35 and into the buffer solution 36 in reservoir 33 during separation. Outlet end 40 is electrically connected, as hereinafter described, to form a closed electrical circuit for the first high voltage system 16A.

Capillary 20 can be fabricated in the form of any capillary structure capable of effecting the capillary zone electrophoretic process. Particularly, however, nonconductive materials such as glass, fused silica, TEFLON® and the like are preferred materials of construction of such capillary. Preferably, the capillary has a length of 20 to 500 centimeters and has an inside diameter which ordinarily ranges from about 25 uM up to about 250 uM, although a wider range of dimensions is feasible.

Capillary tube 20 has joined to its outlet end 40 a second high voltage input system 16B, including a second high voltage power supply 24. This system 16B is grounded or biased at a selected voltage above ground to complete a first closed circuit for high voltage supply 18, as shown in FIG. 2A. The electrical connection at the capillary outlet end serves as both the electrode for the CZE step and also as the spray needle for the electrospray step. More specifically, the system 16B forms a completed circuit with high voltage supply 24 through a physical connection with a high voltage line 42. Thus, high voltage power supply 24 is grounded at one end 44 and is connected at its other end through high voltage line 42 to outlet end 40. This electrical connection also forms circuit 16B, which enables the analyte to be electrosprayed upon application of a second high voltage from voltage supply 24 through line 42.

A large voltage drop is applied from the inlet end 39 to the outlet end 40 of the capillary to enable electrophoretic separation of the analyte solution 36. The high voltage also causes a bulk electroosmotic flow of buffer towards the capillary outlet 40. The high voltage is applied from power supply 18 through microsampling arm 34 into the reservoir 33. The voltage drop along the capillary is the difference between the voltage from supply 18 and the voltage from supply 24. The voltage drop draws the buffer solution 36 into capillary 20. It also causes solution 36 to be electrophoretically separated into its individual molecular constituents as they pass at differing levels of electrophoretic mobility from inlet end 39 to outlet end 40. The amount of voltage provided from power supply 18 into the sample analyte solution 36 ranges typically from about 5 kilovolts DC up to about 100 kilovolts DC. If ions of both positive and negative electrophoretic mobility are to be analyzed, the electroosmotic flow must be sufficiently large to offset the electrophoretic motion in the opposite direction, so that all analytes of interest move towards the capillary exit. It should be noted that nonconducting capillaries can form an electrical double layer with electroosmotic flow in a direction and rate that depends on the surface or any surface treatment of the capillary. In such a situation the polarity of the voltages required for CZE separation may be reversed.

Figure 3:
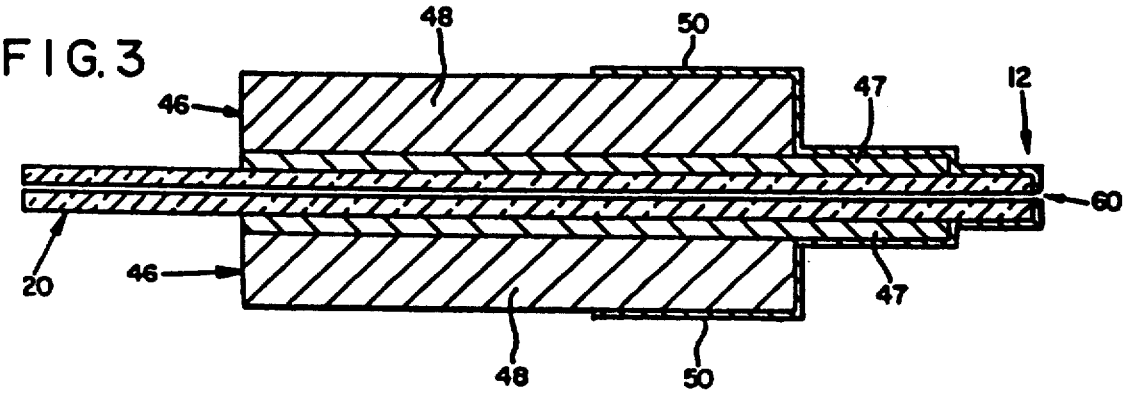
FIG. 3 is a schematic cross-sectional view of the capillary zone electrophoresis cathode which also serves as the electrospray needle in the apparatus of FIG. 2.

The basis of the invention includes forming a completed electrical contact at or near the capillary exit 40 without immersing it in a beaker of buffer solution. Referring to FIG. 3, a schematic illustration of the capillary zone electrophoresis electrode which serves as the electrospray needle, a novel CZE-electrospray interface (ESI) system 12 is provided. The outlet end 40 of capillary 20 has a conductive stainless steel capillary sheath 46 located concentrically thereabout. The sheath 46 comprises respective inner section 47 and outer section 48 joined one to the other. Sheath 46 is attached to capillary 20 by an adhesive such as an epoxy resin or the like. The sheath 46 is physically connected to high voltage power supply 24 by means of a copper conductive wire 42 (see FIGS. 2 and 2A). A conductive metal-plated end section 50 is plated concentrically about the exit of the outlet end 40, including the exit portions of respective sheath sections 47 and 48, to form conductive tip 60 contacting the electrophoretically separated solution 36.

In one form of the invention, a metal coating is sputtered onto the respective exit portion of sheath 46 and outlet end 40 so that electrical contact is directly made with the eluent at tip 60 as soon as it emanates from the exit of nonconductive fused silica capillary 20. Typically, a metal such as gold, silver, or platinum is employed for this purpose. Preferably, the conductive tip is formed so that the dead volume after completion of the electrical circuits is minimized and there is virtually no flow turbulence within capillary 20 and, therefore, no substantial contribution to band broadening (or loss of separation) of the analyte sample. The ability to minimize flow turbulence, and thereby maintain continuous flow of the eluent 36 in capillary 20, is dependent upon capillary diameter and length. For example, the effective dead volume for a 100 um. i.d. capillary 1M in length should be not more than about 10 nL, and preferably less than about 1 nL.

The electrical contact can be formed in other ways, which include (1) joining a metal capillary to the nonconductive CZE capillary; or (2) electrical contact through a small conductive capillary segment near the capillary exit. The latter can be done in numerous ways, but approaches that minimize the dead volume after the electrical contact are necessary so as to avoid loss of separation efficiency.

High voltage system 16B creates an electrical potential between the capillary tip 60 and eluent 36 and the collection or detection apparatus, such as the counter electrode 26 of the mass spectrometer shown in FIGS. 2 and 2A. The purpose is to produce an electric field resulting in the desired electrospray process.

Depending upon whether positively or negatively charged constituents are to be desirably produced by subsequent electrospraying, either a positive or a negative (+/−) voltage is applied to the capillary end 40 relative to the counter electrode (sampling orifice) 26. Voltages of about +/−2,000 to 8,000 volts DC can generally be used, with a voltage of about +/−3,000 to 4,000 volts DC being preferred depending upon the distance to the counter electrode. The resultant electric field causes the eluent 36 to be discharged (electrosprayed) in airspace 62 from the conductive tip 60 of capillary tube 20. This produces a fine spray 64 of electrically charged droplets including gaseous ions, solvent and solvent-carrying analyte material, having a charge polarity determined by the field.

Figure 7:
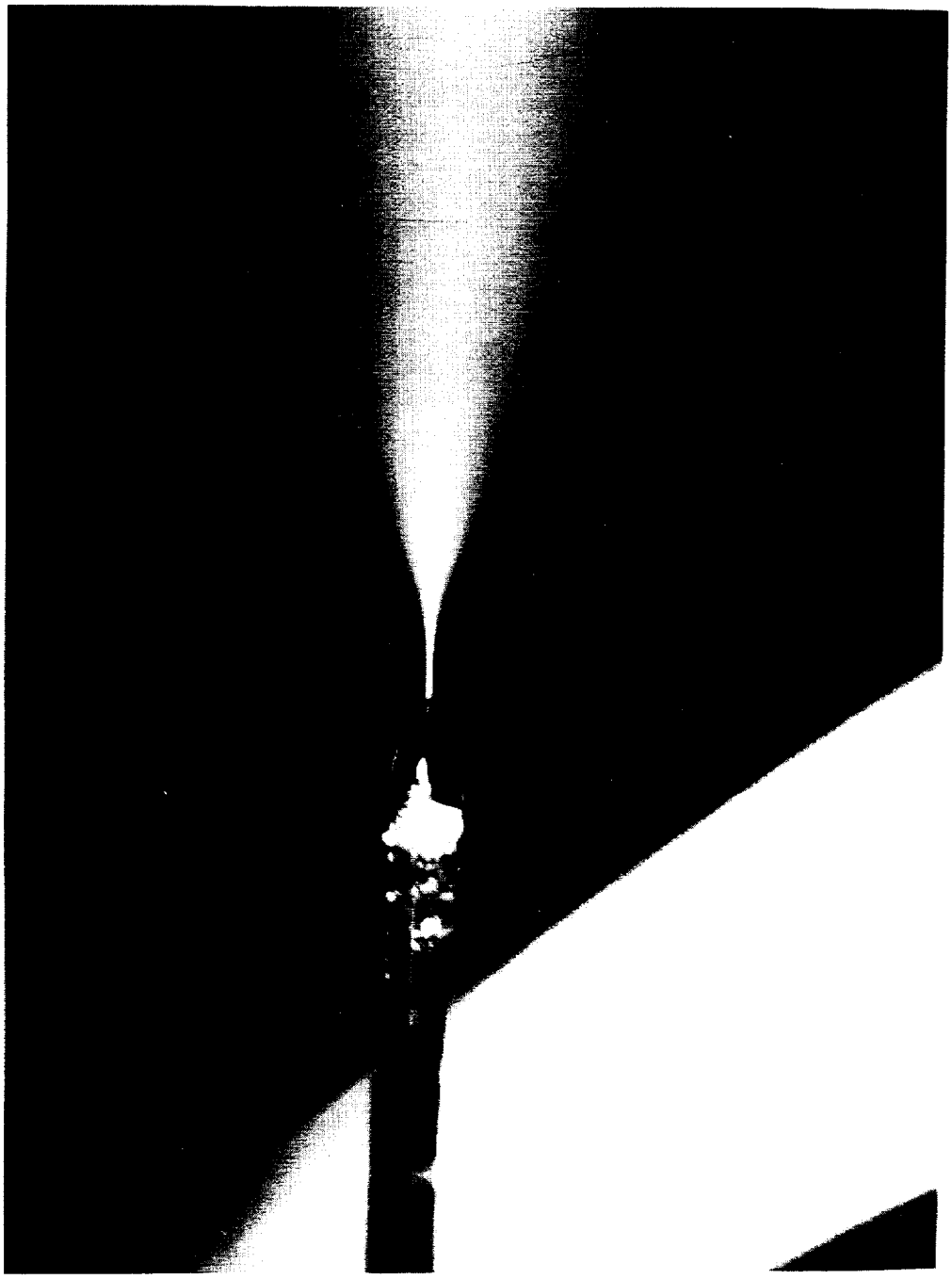
FIG. 7 is a photograph of a fully developed electrospray produced at the end of a fused silica capillary similar to that of FIG. 3.

These electrospray droplets are attracted towards counterelectrode 26, which has sampling provisions, i.e., an orifice 63, for on-line detection or off-line collection device, by the electric field created by high voltage system B. FIG. 7 shows a photograph of a fully developed electrospray flowing from capillary outlet 40.

Electrospray Analysis

Analysis of the electrosprayed eluent 64 can be conducted employing any on-line detection or off-line collection equipment capable of analyzing the molecular or atomic constituents of the eluent. Alternative analysis techniques are further described hereinafter. Preferably, molecular analysis by on-line detection techniques, and more preferably, by mass spectrometry, is employed as next described.

In on-line detection gaseous phase analysis, hereinafter described, a counter-current flow of hot gas 68 is typically used to assist solvent vaporization of the spray 64 of charged droplets. Thus, vapor is removed from electrospray source region 62, which is at approximately atmospheric pressure. The resultant droplets have nearly uniform size, similar charge, and produce gaseous molecular ions.

As depicted in FIG. 2, a ring member 66 is employed to heat the gas in the airspace which in turn heats the exiting electrosprayed analyte eluent 64. Generally, gas temperatures of from about 50° C. up to about 120° C. can be employed for this purpose but a wider range of temperatures would be usable depending on flow rate.

The countercurrent gas flow 68 of inert or reactive gases can be employed, alone or in combination with the previously-described thermal heating for desolvating the spray droplets. Typical inert gases include nitrogen, helium and the like, and typical reactive gases include ammonia, oxygen and the like. Countercurrent gas flows are directed through chamber 69 so as to impinge the electrosprayed analyte eluent 64 within the airspace 62. Typical gas flow rates of from about 0.1 liter per minute, up to about 20 liters per minute, can be employed for this purpose.

Operation of CZE-Electrospray Interface

The method and system of this invention is broadly applicable to the analysis of any material soluble in water or polar solvents, particular ionized or partially ionized species. Compounds amenable to this process include normally neutral compounds on which a charge can be induced by manipulation of buffer solution composition and neutral compounds separated by buffer solutions containing micellar phases or microemulsions by partitioning between the bulk liquid and micelle phases. This includes materials separable by electrokinetic chromatography, as well as those separable by CZE and capillary isotachophoresis. In general, complete mixtures of positive, negative and neutral constituents in solution are amenable to separation and analysis by the subject invention. This method and system is more particularly applicable to the separation of organic, inorganic, and bio-organic molecules soluble in aqueous solutions. Nonaqueous solvents may also be used. Some organic solvents, especially those with some ionic characteristics, or those that can be seeded or mixed with ionic components, are also applicable. With respect to the solvent portion of the analyte sample solution 36, any solvent is suitable for use herein as long as it exhibits at least a minimum conductivity. The solution 36 preferably has a minimum surface tension, if used with gas phase ion detection methods, in order to permit maximum desolvation on subsequent electrospraying. Thus, compounds ranging from aqueous to organic solvents to mixtures of solvent components may be employed if a certain minimum ionic strength of the analyte solutions formed are achieved. Aqueous sample solutions preferably include a buffering agent. These solutions are preferably provided at concentrations below about 0.01M.

Buffer materials are also required for most CZE media. The buffer and solvent mixtures are chosen according to the sample employed in the electrophoretic process relative to the buffer selected. The buffer portion of solution 36 provides a number of important properties. First, the buffer imparts ionic strength for enhancing conductivity and minimizing field effects which distort separation of the individual constituents. It also provides a stable pH medium in which the solution is stabilized and effective constituent separations can be performed at different electrophoretic mobility levels. A solution is formed with a sufficient level of conductivity that subsequent electrospraying can be effectively performed. Buffer concentrations preferably ranging from about $10^{-6}$ to about $10^{-2}$ molar are particularly useful in this invention. Typical compounds employed as buffers include ionic salts such as ammonium salts, inorganic salts such as sodium and potassium chloride, and organic salts such as potassium phthalate.

Regarding electrical currents present in the system, it should be noted that a high voltage-low current relationship is typically maintained in the system. Currents which will facilitate the system and method of this invention and which can provide maximum separation of the analyte constituents are employed. Although the current is dependent upon such variables as the ionic strength of the solution, the capillary column length and inside diameter of the capillary, current is preferably maintained at or below the 100 uA level. The current is typically directly proportional to voltage and the maximum voltage is usually selected so that heating of the buffer solution in the capillary is minimized, since heating results in convective flow which degrades separation efficiency.

In order to analyze the molecular constituents according to the method and system of the present invention, sample solution 36 is electrophoretically separated into its molecular constituents. The use of electrophoresis according to the teachings of the subject invention facilitates high efficiency separation or analysis of complex materials. First, voltage is briefly applied to the analyte sample solution 36 and migration of a small amount of the sample solution into a capillary 20 is achieved due primarily to electroosmotic flow. The buffer solution reservoir 33 is then introduced into the sampling box 30, the capillary is removed from the sample reservoir and introduced into the buffer reservoir, high voltage is applied thereto, and electrophoresis proceeds.

Electroosmosis is caused by the migration of ions, from the diffusive layer of the electrical double layer at the capillary surface, under the influence of an electrical field imposed tangentially to the surface. The ions present in the analyte will then migrate towards the oppositely charged electrode carrying the capillary contents with them. The electroosmotic flow is sufficiently fast that positively charged ions, neutral molecular compounds, and negatively charged ions elute in short times, typically about 5–30 minutes for a 1M capillary. In a positive voltage gradient, positive ions will have the largest net mobilities and will elute first since they are repelled by the high voltage anode, resulting in positive electrophoretic mobilities, and also will be carried by the electroosmotic bulk flow of the solvent. Negative ions having the largest negative electrophoretic mobilities will elute last. Negative ions with very high electrophoretic mobilities may never elute from the column if the electroosmotic flow is not sufficiently fast, but usually conditions can be varied so that the electroosmotic mobility is always larger than the analyte's electrophoretic mobility.

Therefore, the migration time through the capillary column 20 is for the most part determined by a combination of the capillary length, the molecule's electrophoretic mobility in the electric field, the electric field strength, and the electroosmotic flow of the supporting buffer solution. The various constituents forming analyte sample 36 have different relative electrophoretic mobilities. These differences in electrophoretic mobility produce a dissimilar rate of migration of the molecular constituents from the inlet 39 to the outlet 40 of capillary 20. This results in an effective, high efficiency separation of these different molecular constituents with respect to time so that the identity and quantity of each constituent can be individually and analytically determined or collected.

In defining the optimum conditions for electrophoretic flow of analyte eluent 36 from inlet 39 to outlet 40, the following are some of the preferred conditions: a minimum metal surface contact or other electrical contact between the analyte flowing in the capillary to complete an electrical circuit near the point of electrospray formation, a substantially constant voltage drop from inlet 39 to outlet 40, and a continuous inner flow surface, having minimum discontinuous surface areas and substantially no dead volume is present, so that electroosmotic flow of the analyte eluent 36 in the capillary is created with a minimum introduction of any turbulent effects.

The electrospray of the subject invention can be used in both the positive and negative ionization modes, although a small addition of oxygen or other electron scavenger to the bath gas is useful for negative ion production to avoid electrical breakdown.

For mass spectrometric analysis, this atmospheric pressure ion source is then typically followed by a molecular beam sampling apparatus consisting of a nozzle-skimmer arrangement with an RF only quadrupole field or ion lens system for ion focusing and a quadrupole mass spectrometer for mass analysis and detection. Other mass-spectrometer inlet designs are feasible. For example, nonconductive capillaries can be used as disclosed in Whitehouse, C. M., et al., "Electrospray Interface for Liquid Chromatographs and Mass Spectrometers," Analytical Chemistry, Vol. 57, pp. 675–679 (1985).

In the preferred form of this invention, the electrosprayed droplets are allowed to continually divide and evaporate at near atmospheric pressure to form gaseous ions of analyte constituents employing electrospray techniques similar to those described in U.S. Pat. No. 4,209,696 and EPA No. 84302751.7. The solution flow in the capillary results preferably from electroosmotic flow rather than any pressure drop, so that separation efficiency is not degraded. Thus, spray 64 is formed without substantial distortion of the electropherogram thereby permitting analysis by numerous analytical detectors.

The electrospray process utilized for mass spectrometric detection is similar to that developed by previous workers. As the droplets are formed by the electrospray process, desolvation of the solvent from the droplets begins to occur, and the analyte constituent passes from the liquid phase into the gaseous phase, the gaseous phase including gaseous ions of the analyte constituents. As the droplets move away from outlet 40, they continually decrease in size and their mass-to-charge ratios continually shrinks until an ionic vapor phase stream is formed which is capable of detection by mass spectrometry. Desolvation of the solvent from its association with the droplets can be facilitated thermally and/or by countercurrent gas flow. Electrospraying includes processes which involve electric fields, and may include concurrent utilization of nebulizing gases or heating methods.

In any case, the desolvated vapor phase ions produced, along with the remaining portion of the analyte present within airspace 62, are conveyed to a mass spectrometer for analyzing the identity and quantity of the individual constituents contained in the analyte sample.

Improvements In Mass Spectrometry For CZE-Mass Spectrometry System

Certain features which improve or facilitate analysis using mass spectrometry have also been uncovered with respect to the analysis of electrosprayed eluent 64. These include, for example, the use of an RF only lens in the first vacuum region of the mass spectrometer. These lenses are known to provide nearly 100 percent containment of ions in triple, quadrupole mass spectrometers, where the lens is operated in an intermediate vacuum of about $5\times10^{-4}$ torr, which is similar to the pressures used in the first vacuum region of the CZE-MS system interface. This RF only lens also acts as a high pass mass filter allowing only ions above a preselected mass of interest to pass into the mass analyzer. This cleansing effect (since high ion currents are to be expected from the buffer employed at low masses) provides spectra which are potentially free of space charge effects created when high ion currents containing ions of no interest to the analyst enter the normal quadrupole mass analyzer and are to be rejected during mass analysis. Quadrupole devices are mass analyzers in the form of mass-to-charge separators.

A well-coupled RF-RF/DC pair of quadrupole lenses is also employed to minimize the fringe field effects observed when the lens combination is DC-RF/DC. This serves to maximize ion transmission into the mass analyzer.

Finally, the use of quartz inlet capillaries to transmit ions from the atmospheric pressure electrospray ionization source is a feasible alternative to the nozzle-skimmer introduction method which allows the direct injection of transmitted ions into the RF only quadrupole.

Alternative Analytical Applications

The electrospray interface also provides a basis for combining CZE separations with other on-line analysis techniques. In these methods the electrospray is sampled so that either the small liquid droplets or gas phase ions are introduced into an analytical or detection device. Thus, this invention includes the combination of free zone electrophoresis (and variations which include electrokinetic chromatography and isotachophoresis) separation methods, using electrospray, with other detection methods which include:

1. flame ionization detection;
2. elemental analysis by inductively-coupled plasma or microwave plasma atomic emission for elemental analysis;
3. ion mobility detection;
4. photo ionization detection;
5. element-specific ionization detection;
6. electron capture detection;
7. surface-sensitive analytical methods;
8. infrared analysis of electrosprayed deposits.

The common feature of all the above analysis methods is that a gaseous or aerosol sample is required. The electrospray process produces such a gas or aerosol which may be interfaced to these detection devices. Each analysis method requires somewhat different methods for sampling the electrospray. However, the methods are such that someone reasonably skilled in the above techniques, given the information disclosed herein, could successfully combine CZE with the selected analytical method. It should be noted that some methods will present difficulties due to limited sensitivities, and thus may impose some limitations upon the practice of CZE (such as the use of a larger than optimum sample that may degrade separation efficiency) or the analytical detection method.

Off-line collection or analysis methods are also feasible using the electrospray. In these methods the electrospray is collected on a solid or liquid surface. The surface can be moved so that the temporal distribution of separated analytes is deposited on the surface as a spatial distribution. The separated sample collected on the surface can be utilized for other off-line analysis methods or other purposes where only a small sample is required. The spatially distributed material can also be analyzed by analytical methods which are compatible with solid samples on surfaces. These analytical methods include:

1. mass spectrometry using a moving ribbon or belt with ionization methods which include ion or atom bombardment;
2. infrared analysis of surfaces;
3. any surface-sensitive analytical method.

EXAMPLE 1

Using the CZE-mass spectrometer system specifically depicted in FIG. 2, the identity and quantity of an analyte sample was determined.

CZE was carried out using a 0–60 kV dc power supply, Glassman High Voltage Inc. (Whitehouse Station, N.J.) Model LG60P2.5. The high voltage electrode and capillary end (anode) and solution vials were contained in an insulating sampling box with a remote controlled sampling arm and injection timer to facilitate the interchange and injection of solutions. Fused silica capillaries, 100 um i.d. and 100 cm long, from Polymicro Technologies, Inc. (Phoenix, AZ), were used in all experiments without further treatment. The cathode (low voltage end) of the fused silica capillary was terminated in a stainless steel capillary sheath, 300 um i.d. and 450 um o.d. (see FIG. 3). The sheath potential was controlled with a 0 to 5 kV dc power supply and functions as both the CZE cathode and electrospray needle (see FIG. 2A).

Electrospray ionization was carried out at atmospheric pressure in a 2.54 cm long by 2.29 cm i.d. stainless steel cylinder. The cylinder terminated in an electrically biased (190 V dc) focusing ring 44 with a 0.475 cm aperture. The ion sampling orifice (or nozzle) 63 had a 0.5 mm i.d. orifice, was made from copper, which was in contact with a copper cylinder at ground potential. This cylinder surrounded the electrospray assembly and was heated to 60° C. by a system of cartridge heaters (not shown). The electrospray needle, focusing ring 66, and ion sampling nozzle 63 were disposed concentric with the mass analyzer. These components could be positioned independently relative to the fixed skimmer 70 (with the aid of linear motion drives), even while high voltage is on, in order to maximize ion formation and transmission. A flow of $N_2$ forming a gas curtain, at a flow rate of 2.5 L/min, is fed between the focusing ring 66 and the nozzle 63 and directed so as to flow counter to the electrospray to aid in the desolvation process.

The vacuum system consisted of a three stage differentially pumped chamber, although many different arrangements are feasible. The first stage allows for a supersonic beam expansion through the ion sampling nozzle 63. This region is pumped to 0.85 Torr by a 150 L/s roots blower. A portion of the supersonic beam is sampled by a 1.2 mm i.d. beam skimmer, Beam Dynamics, Inc. (Minneapolis, MN), Model 1. The second differentially pumped stage houses a 22 cm long, 0.95 cm diameter quadrupole filter 72. This quadrupole is operated in the RF only mode with a −1.8 V dc rod bias and acts as an ion lens which facilitates ion transmission to the analysis quadrupole. The pressure in this region is maintained at $10^{-4}$ to $10^{-5}$ Torr with a 1500 L/s turbomolecular pump. Another version of this instrument substituted an integral cyro-pump which provided a pumping speed of approximately 50,000 L/S and allowed larger orifice and skimmer diameters. An electrically isolated stainless steel plate (−28 V dc), with a 0.635 cm i.d. orifice, allows the mass spectrometer chamber to be maintained at $2\times10^{-6}$ Torr using a 550 L/s turbomolecular pump. The 2000 amu range quadrupole mass filter, Extrel Co. (Pittsburgh, Pa.), Model CQPS1HV, and a channeltron electron multiplier 74, Detector Technologies, Inc. (Brookfield, Mass.), Model 203, operated in the analog mode. Data acquisition and mass scanning was performed with a Teknivent Corp. (St. Louis, Mo.) Model 1050 interface-IBM PC/XT based system. Additional operational parameters were as follows: applied voltage of 40,000 V dc, electrospray voltage of 3,000 V dc, focus ring voltage of 190 V dc, $N_2$ flow rate of 2.5 L/min, source temperature of 60° C., RF only quadrupole dc bias of −1.8 V dc, and an ion entrance aperture of −28 V dc.

Injection of samples onto the CZE capillary was performed using the previously-described electromigration technique of Jorgenson et al. In electromigration, the anode end 39 of the column is introduced into the analyte solution, the injection voltage is turned on for a predetermined amount of time, the voltage is turned off and the buffer replaced; the CZE applied voltage ($V_{app}$=40,000 V dc) and electrospray voltage ($V_{ESI}$ voltage=3000 V dc) are then turned on and the separation is allowed to continue. (The CZE voltage $V_{CZE}$) here refers to the voltage drop across the CZE column which has been modified from the traditional sense because the cathode is maintained at the electrospray voltage; thus $V_{CZE}=V_{app}-V_{ESI}$.)

A (50-50) water-methanol with $10^{-4}$M KCl was used as the separation and electrospray medium. It was observed that water-methanol provides a considerable electroosmotic mobility ($3.6\times10^{-4}$ cm$^2$/V s) with the fused silica capillary. Thus, positively ionized compounds elute in less than 12.5 minutes from a 100 cm long column (with $V_{CZE}$=37,000 V).

EXAMPLE 1: RESULTS AND DISCUSSION

Five ammonium salts were tested: tetramethyl ammonium bromide, tetraethyl ammonium perchlorate, tetrapropyl ammonium hydroxide, tetrabutyl ammonium hydroxide, and trimethyl phenyl ammonium iodide. These quaternary ammonium salts all give good electrospray signals with the dominant peak in the mass spectrum being the quaternary ammonium cation.

Figure 1:
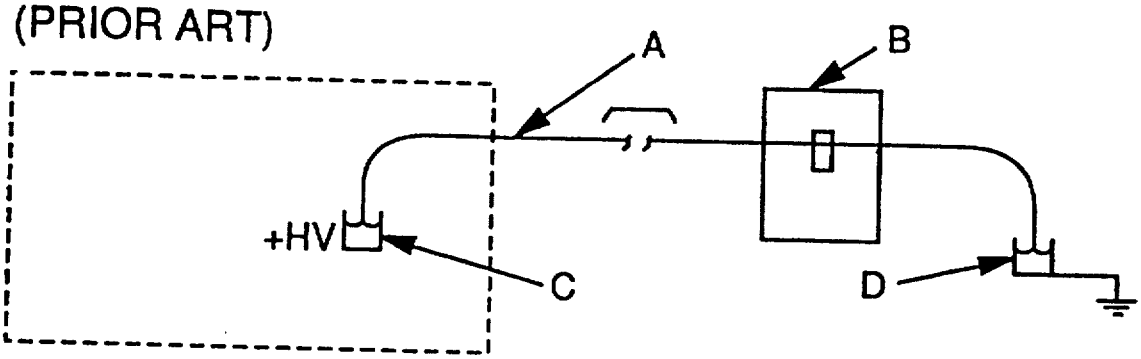
FIG. 1 (PRIOR ART)
FIG. 1 is a schematic illustration of conventional apparatus used for capillary zone electrophoresis.
Figure 4:
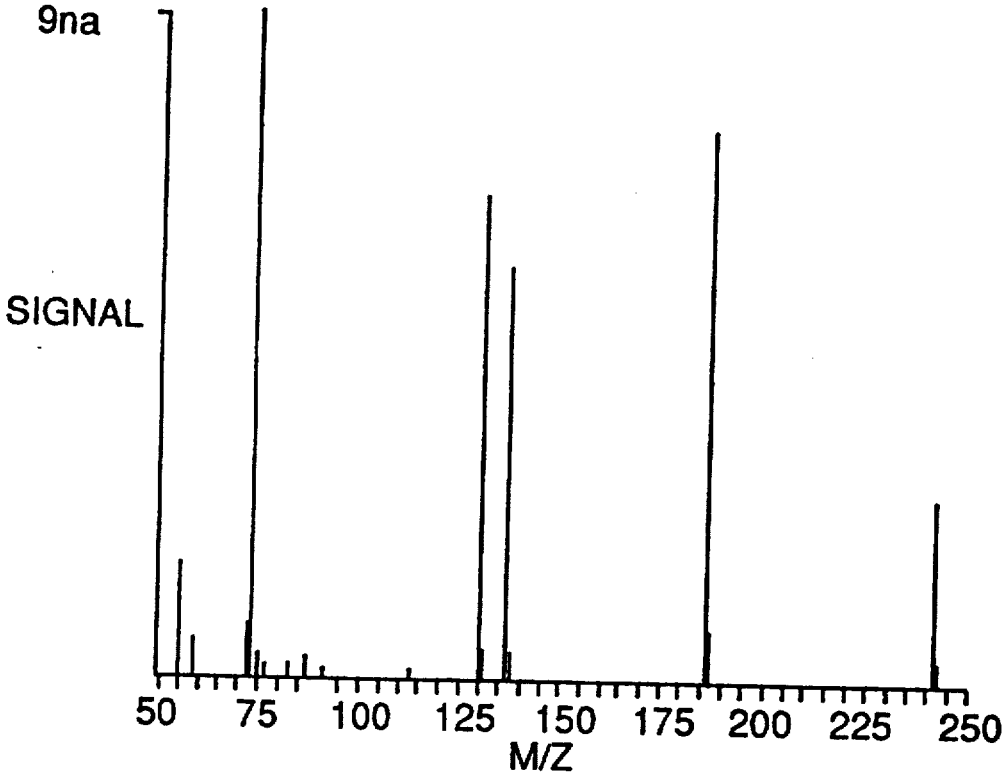
FIG. 4 is an electrospray ionization mass spectrum of a mixture of five quaternary ammonium salts at $10^{-5}$ M concentration introduced by continuous electromigration.

FIG. 4 shows the electrospray ionization mass spectrum for the five components injected at $10^{-5}$M concentration by continuous electromigration without CZE separation. The dominant peaks are due to the quaternary ammonium cations of: tetramethyl ammonium bromide (m/z-74); tetraethyl ammonium perchlorate (m/z-130); trimethyl phenyl ammonium iodide (m/z=136); tetrapropyl ammonium hydroxide (m/z=186); tetrabutyl ammonium hydroxide (m/z=242); and a background peak due to Na-MeOH+(m/z=55).

Figure 5:
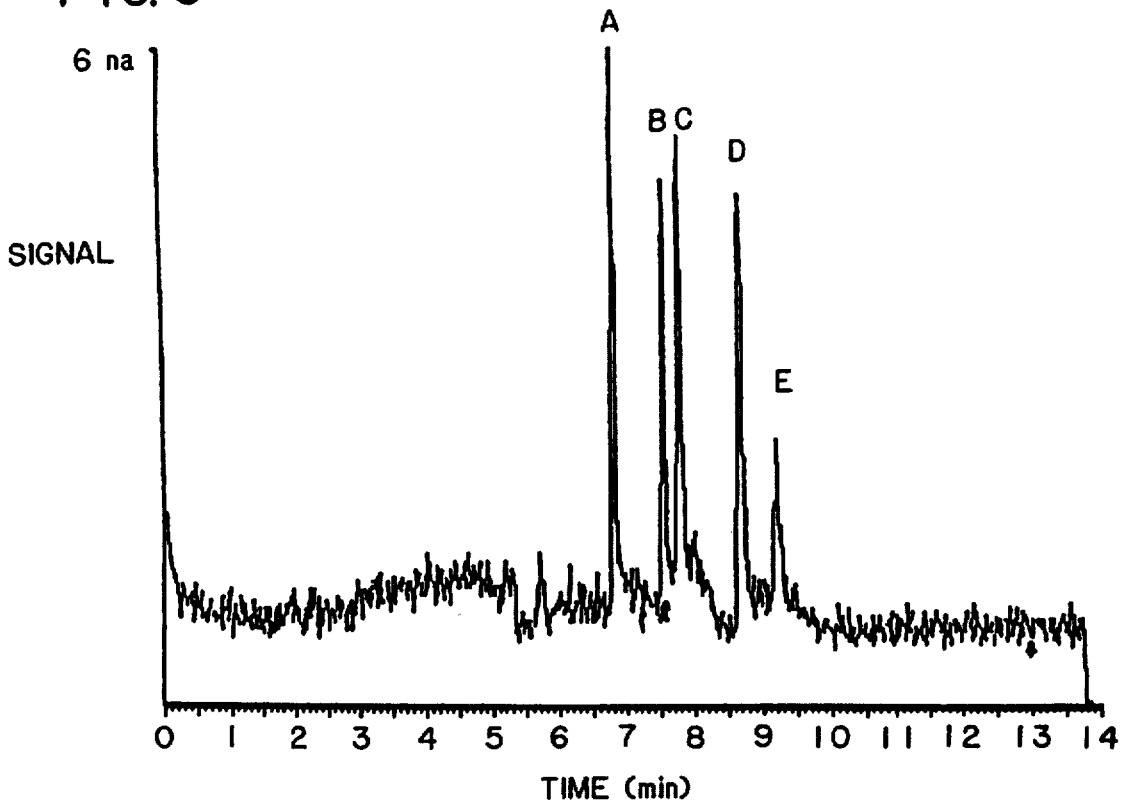
FIG. 5 is an electropherogram, obtained by CZE-MS in accordance with the invention, of five quaternary ammonium salts, at $10^{-6}$M (14–17 femtomole injection) concentration.

The first CZE-MS separation of such a mixture, taken under multiple ion monitoring of the corresponding quaternary ammonium cation peaks, is shown in FIG. 5. FIG. 5 is an electropherogram of five quaternary ammonium salts, at $10^{-6}$M (14–17 femtomole injection) concentration, obtained by CZE-MS: (A) tetramethyl ammonium bromide; (B) trimethyl phenyl ammonium iodide; (C) tetraethyl ammonium perchlorate; (D) tetrapropyl ammonium hydroxide; (E) tetrabutyl ammonium hydroxide. The amounts injected for the quaternary ammonium salts, 14–17 femtomoles, gave single ion electropherograms with good peak shapes and signal/noise ratios.

Figure 6:
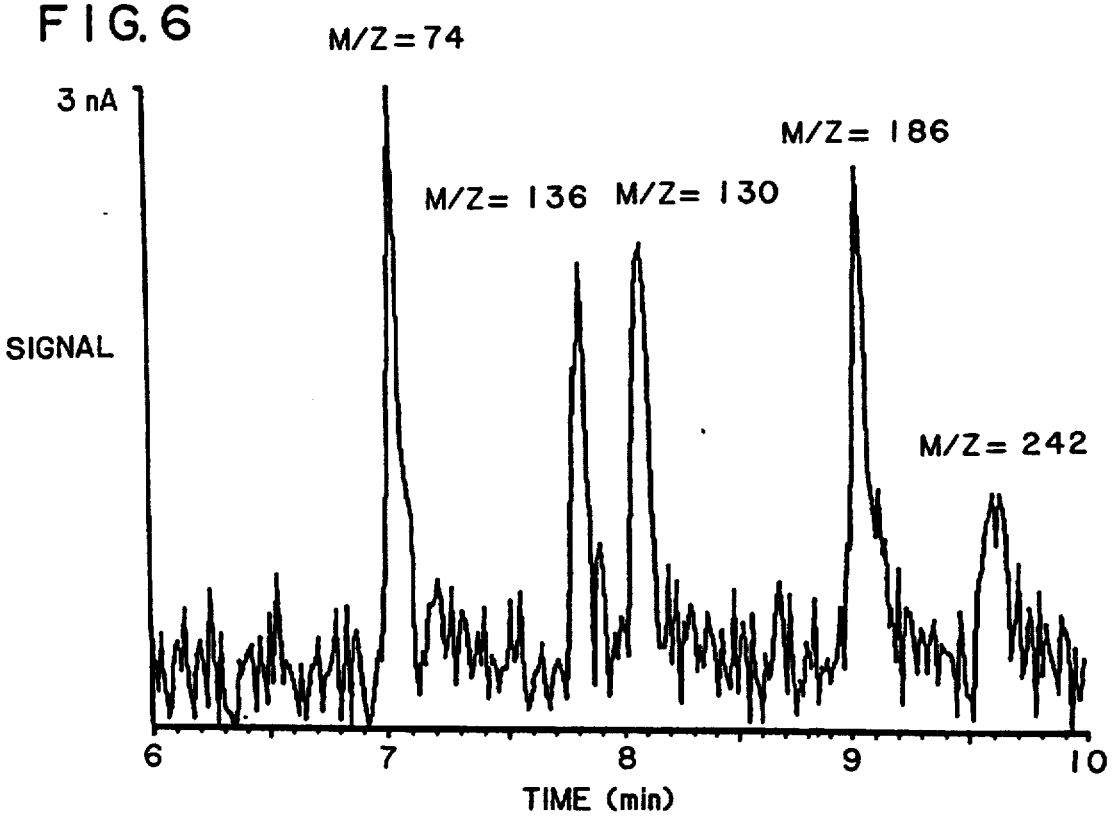
FIG. 6 is an electropherogram, obtained by CZE-MS in accordance with the invention, of five quaternary ammonium salts, at $10^{-7}$M (0.7–0.9 femtomole injection) concentration.

FIG. 6 is an electropherogram of five quaternary ammonium salts, at $10^{-7}$M (0.7–0.9 femtomole injection) concentration, obtained by CZE-MS: tetramethyl ammonium bromide (m/z−74); tetraethyl ammonium perchlorate (m/z−130); trimethyl phenyl ammonium iodide (m/z 136); tetrapropyl ammonium hydroxide (m/x=186); tetrabutyl ammonium hydroxide (m/z−242). FIG. 6 shows the same separation obtained for a 0.7–0.9 femtomole injection, obtained by decreasing $V_i$ to 0,000 V, and C to $10^{-7}$M.

Though the separation efficiencies in FIG. 5 vary from 26,000 and 100,000 theoretical plates, they are increased to between 35,000 and 140,000 theoretical plates in FIG. 6. Such increases in efficiency with decrease in sample concentration and size suggest further improvement can be obtained with higher buffer ionic strength and either smaller diameter or longer capillaries.

As described earlier, the cathode need not be in a buffer reservoir, but only biased negative with respect to the anode. Thus, a metallized segment of capillary tubing or other electrical contact with the buffer provides the essential control of the electric field. This approach (necessary for mass spectrometric interfacing) does not alter the electroosmotic flow, if a pressure drop along the length of the capillary is avoided, at least to an extent that is detectable with fluorescence detection just prior to the electrospray. The success of this approach is further supported by the high efficiency separations presented. On the basis of these results, electrospray ionization appears to provide an ideal interface for the combination of a highly efficient separation technique, CZE, with the sensitive and highly specific detector provided in the mass spectrometer.

Complex mixtures of compounds pose a problem even to the trained mass spectroscopist because the identity and the quantity of each constituent is not readily ascertainable.

Figure 8:
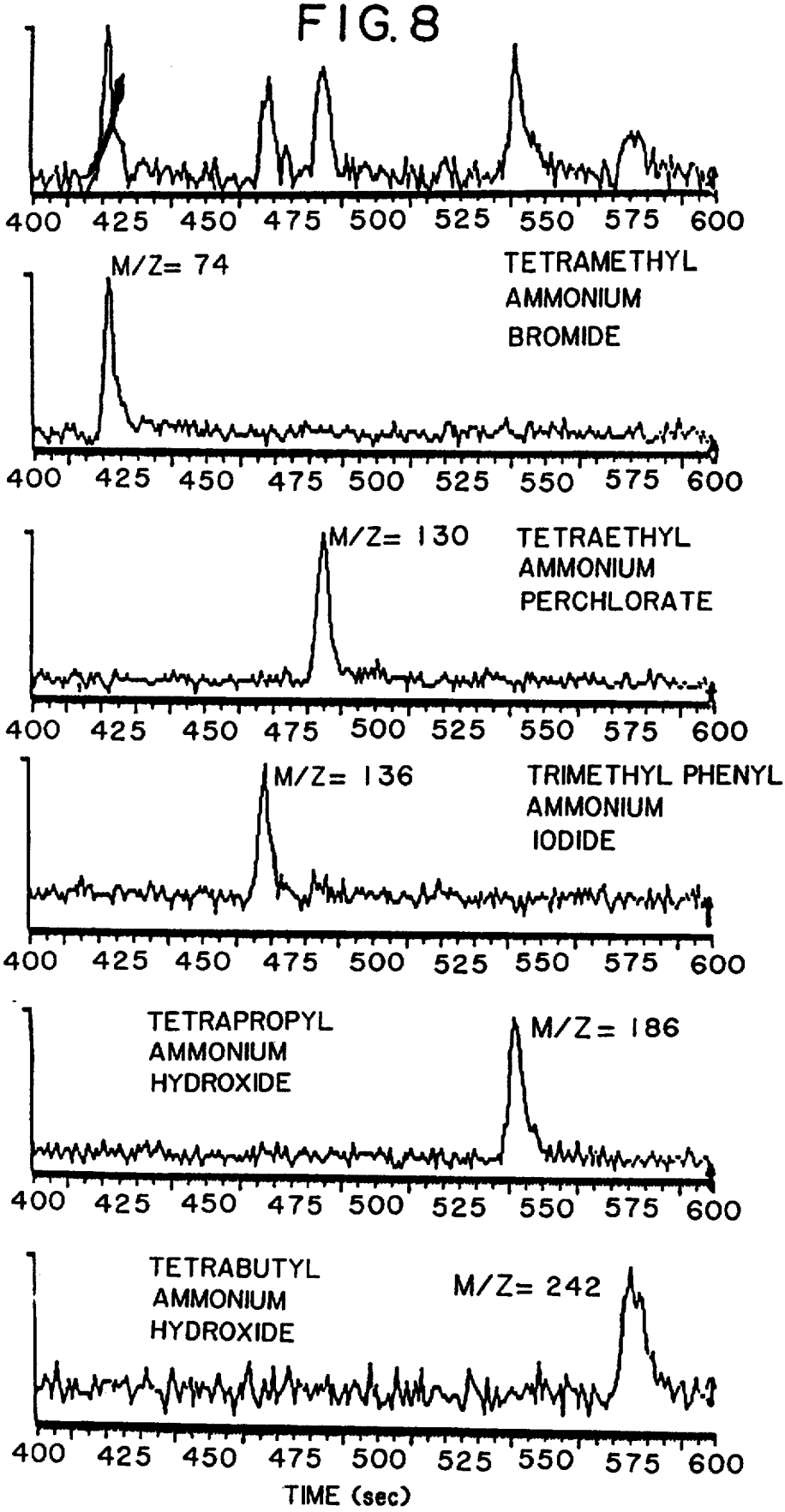
FIG. 8 is a set of total ion and single-ion electropherograms of five quaternary ammonium salts obtained by CZE-MS in accordance with invention.
Figure 9:
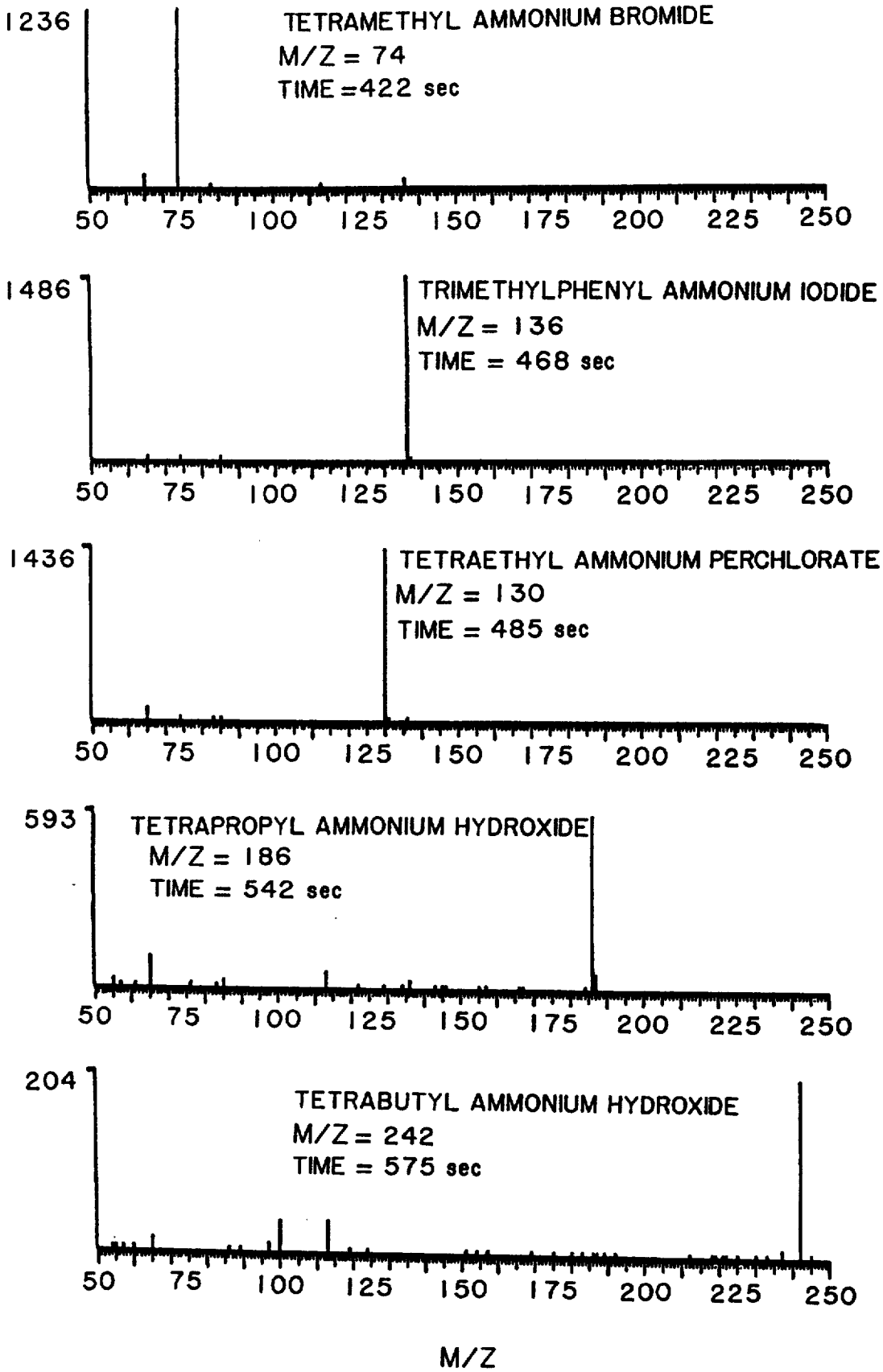
FIG. 9 is a set of mass spectra of CZE-MS separated compounds of the quaternary ammonium salt mixture of the electropherogram of FIG. 6.

Using the system and method of the present invention, a series of electropherograms of the abovedescribed five quaternary ammonium salts were produced (see FIG. 8). These electropherograms are obtained by tracing the ion current for a particular ion of mass m/z throughout the separation process (over time). Single mass spectra (see FIG. 9) for each of the components to be determined can then be obtained for a particular time in the separation process. These mass spectra are used to identify the molecular weight of the particular component, while the area under the electropherogram peak is used for quantification.

ALTERNATIVE EMBODIMENT WITH SHEATH ELECTRODE FLOW

The CZE-MS interface described previously above has a number of attractive features, including the fact that the effective detection volume is negligible and does not appear to contribute to CZE bandspread. In addition, the electrospray is created directly at the terminus of the CZE capillary, avoiding any post-column region which would contribute to extra-column bandspread (due to laminar flow) or analyte adsorption The previous example of operation of the electrospray interface did not require any additional gas flow for nebulization purposes, as in the "ion spray" configuration of Henion and coworkers described for LC-MS, and the attendant problems associated with the larger droplet size distribution. These problems include the need to sample the electrospray "off-axis", and reduced sensitivity since analyte in larger droplets will not be efficiently ionized. (Bruins, A. P.; Covey, T. R.; Henion, J. D., "Anal. Chem." 1987, 59, 2642–2646.)

The foregoing example of CZE-MS interface does, however, impose significant limitations upon the CZE separation conditions. One restriction is related to the minimum flow rate required for generation of a stable electrospray. The electroosmotic flow rates, in fused silica capillaries relevant to CZE, range from zero to as much as several uL/min, depending upon capillary surface treatment, diameter field gradient, and buffer composition (i.e., ionic strength and pH). Stable electrosprays are increasingly difficult to maintain at flow rates under 0.5 uL/min, and can be perturbed by stray electric fields, mechanical perturbations (e.g., vibration), or minute variations in flow, causing increasingly severe oscillations in performance as flow rate decreases. A second restriction is related to buffer composition. For example, aqueous solutions or buffers with ionic strengths above about $10^{-2}$M cannot be effectively electrosprayed. These restrictions are not as severe as might be assumed since mixtures of alcohols and water can be easily electrosprayed, but can limit application to certain analytes as well as the range of useful CZE conditions. In addition, buffer chemistry can strongly affect the ESI process; certain components may suppress or enhance ionization efficiency, but not necessarily have a desirable effect upon the separation process. A final limitation of our original interface is the necessity of metal deposition at the capillary terminus which provided the electrical contact used to define both the CZE and ESI field gradients. The capillary preparation process is time consuming due to the several steps required for metal deposition and the contact with a surrounding stainless steel sheath used to impart mechanical stability. In addition, the deposited metal slowly erodes and requires replacement after several days of operation.

We have, therefore, developed an improved electrospray ionization interface (ESI) 110, 110A (FIGS. 10–14) and 110B (FIG. 19) for CZE-MS and other applications which removes the limitations of the above-described design. The object of the improved design is to retain the attractive features of the foregoing design (i.e., avoidance of extra-column volumes, a well-behaved electrospray process, etc.) but not to impose any additional limitations upon operation. The improvement replaces the metal contact at the CZE outlet 40 with a thin sheath of flowing electrically-conductive liquid. The net result of this change is that the desired features of our original interface are retained while circumventing previous limitations on CZE flow rate and buffer composition. In addition, these changes provide a qualitative improvement in ESI stability, a design which does not require special treatment of the CZE capillary, and the capability for easy replacement of the CZE capillary. These and other advantages discussed in EXAMPLE 2 below suggest the improved ESI interface would allow much wider application of the CZE-MS method and the basis for extension to other capillary electrophoresis techniques.

EXAMPLE 2

CZE-MS Instrumentation

The system arrangement and instrumentation used for CZE-MS in this example is largely the same as that described above for EXAMPLE 1 and like reference numerals are used in FIGS. 10–13 to indicate similar components. CZE was conducted in a fused silica capillary 20 with electroosmotic sample introduced at a rate of 0.1–1 microliters/min at the high voltage (10 to 50 kV) electrode. The high-voltage region containing the buffer and sample containers 32, 33 is electrically isolated in an interlocked Plexiglas box 30. Untreated 100 um i.d. fused silica capillaries were used for all studies.

As demonstrated previously, operation of both the CZE and ESI requires an uninterrupted electrical contact for the electroosmotically eluting liquid at or near the capillary terminus. In this example, the electrical contact for the buffer at the low voltage (detection) end 40 of the capillary 20 was made by a sheath flow of liquid 116, generally methanol, propanol, acetonitrile or similar, easily electrosprayed substances, as described in the next section. This electrical contact also serves to define the ESI voltage and was typically in the range of 3 to 5 kV. The ESI focusing electrode 26 was typically at +300 V (for positive ion operation). A nozzle-skimmer bias of 80 to 150 V was found to give optimum performance. The skimmer 70 was at ground potential for EXAMPLE 1. A precise pulse-free liquid flow for the sheath electrode flow 116 was provided by a small syringe pump 74, Sage Instruments (Cambridge, MA) Model 341B.

An auxiliary flow of gas 136 was also used on occasion and was introduced at a flow rate of 0.1 to 1 L/min as a sheath around the capillary terminus (ES1 electrode). The purposes of this gas flow were to (1) add oxygen to suppress discharges in the negative ion mode of operation and (2) provide cooling for the sheath liquid flow at high CZE currents. A secondary benefit of this flow was the suppression of gravitationally induced instabilities in the electrospray for buffers which had a tendency to be marginal (i.e., generally too high an ionic strength for the sheath electrode liquid flow rate being used).

Ions created by the ESI process were sampled through a 1 mm orifice (nozzle) 63 into a reduced-pressure region 200 maintained at a presure of 1–10 Torr by a single stage roots blower pumping at 150 liters/-second. The ions entering this region were sampled through a 2 mm diameter orifice of skimmer 70 located 0.5 cm behind the nozzle orifice 63. Ions passing through the skimmer 70 enter a radio frequency (rf) only focusing quadrupole 72. The region 201 containing the quadropole 72 is maintained at a pressure of approximately $10^{-5}$ Torr by differential pumping with a specially-designed Leybold Hereaus cryopump, consisting of a standard compressor and coldhead with a custom cylindrical second stage baffle cooled to approximately 14K, which encloses the quadrupole and provides an effective pumping speed for $N_2$ of >30,000 L/s. The analyzer quadrupole chamber was pumped at 500 L/s with a turbomolecular pump. A single ion lens with an 0.64-cm aperture separates the ion focusing and analysis quadrupole chambers. The pressures in the focusing and analysis chamber were about $1\times10^{-6}$ and $2\times10^{-7}$ Torr, respectively. The counter current flow 68 of $N_2$ (at −70° C.) for desolvation of the electrospray was in the range of 3 to 6 L/min. The mass spectrometer (Extrel Co., Pittsburgh, PA) had a range of m/z 2000.

ESI Interface Design and Construction

Figure 12:
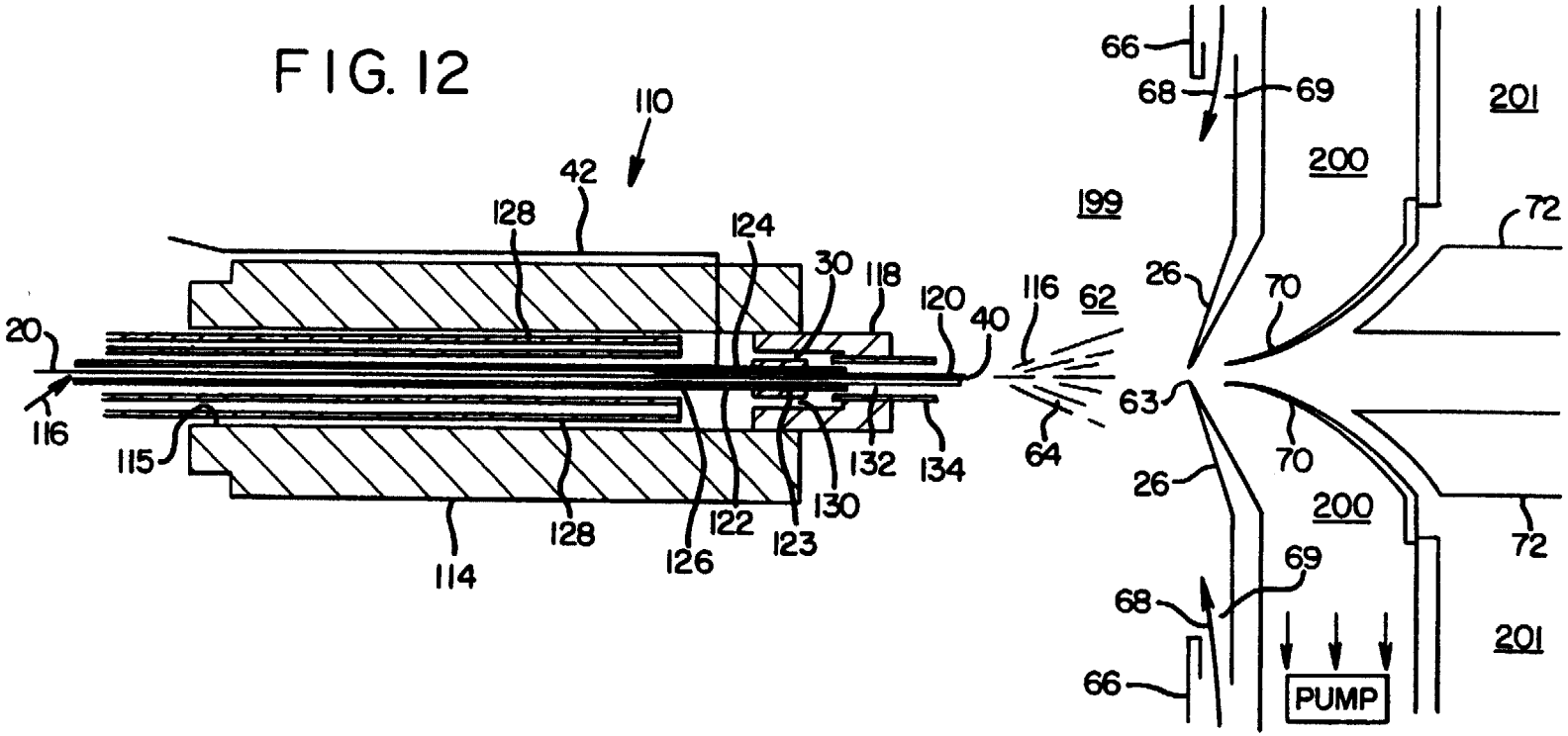
FIG. 12 is a longitudinal cross-sectional view of a second alternate embodiment of a CZE-electrospray-mass-spectrometer interface in accordance with the invention.
Figure 13:
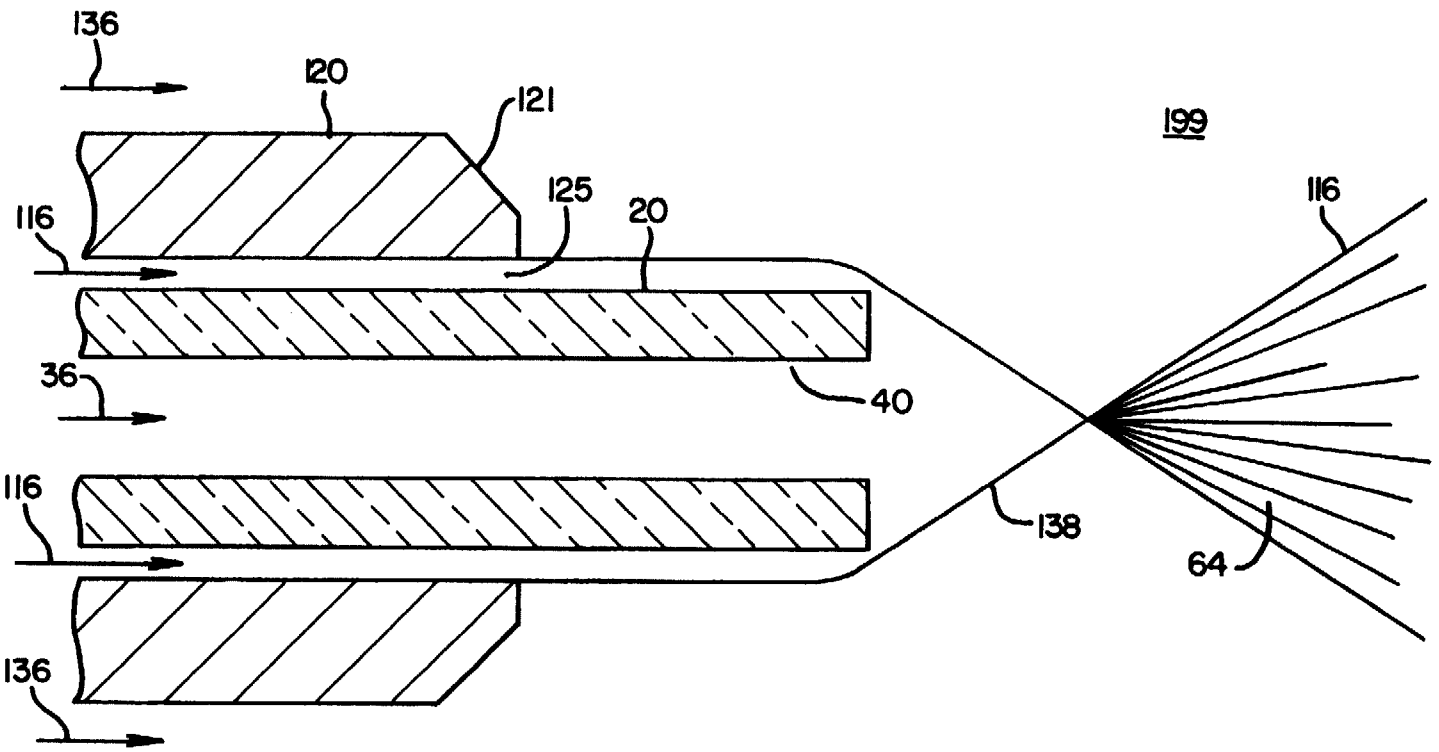
FIG. 13 is an enlarged view showing details of the capillary outlet of FIG. 12.

FIGS. 12 and 13 show a schematic illustration of a preferred version of the sheath electrode ESI interface 110 developed in this work. The ESI probe body 114 is machined from polycarbonate with a central axial channel 115 and mounted in an approximately atmospheric pressure region 199 on custom holders that are movable on a small optical bench rail (not shown). The CZE capillary 20 and a flow of 1–4 microliters/min of sheath liquid 116 are enclosed in a central 1/16 in o.d. Teflon® tube 126 through a Teflon® tee (not shown) outside the probe body. A polycarbonate tip holder 118 carries a conductive electrospray electrode 120 fabricated from a 26 gauge (0.25 mm ID, 0.46 mm o.d.) 3.3 cm long stainless steel (SS) tube soldered concentrically into a 1.9 cm long 21 gauge (0.51 mm ID, 0.81 mm o.d.) SS tube 122. Tube 122 is fitted into an axial bore 123 in the rear of the tip holder and extends rearward into the end of Teflon® tube 126. The ESI end 121 of the SS electrode is machined to about a 45° taper and then electropolished. As the tip holder 118 is screwed axially into the probe body 114, the SS electrode 120 slides over the protruding fused silica CZE capillary 20 forming an annular passage and outlet 125 around the end portion of capillary 20, forming an annular passage and outlet 125, around the end portion of capillary 20, making electrical contact with a spring-loaded, clip-type high voltage connector 124 coupled to conductor 42 and thereby being maintained at ESI voltage of +/−4–7 kv, and snugly fitting into the central Teflon® tube 126 connected to the Teflon® tee. The axial position of the CZE terminus 40 of capillary 20 relative to the SS electrode 120 is easily adjusted bY sliding the capillary in the aforementioned Teflon® tee.

An auxiliary sheath gas flow capability is provided to prevent any deleterious effects due to heating at either the sheath electrode (due to high CZE currents) or the counter current flow of heated nitrogen, although under ordinary operating conditions this provision is not required. The central axial channel 115 contains six 1/16 in. o.d. Teflon® tubes 128 (two shown) that carry nitrogen or oxygen (about 0.1 to 1 L/min.) for the probe gas sheath and the central tube 126 that contains the CZE fused silica capillary 20 and the sheath electrode liquid 116 flowing at 1–10 microliters/min. Two 1/16 in i.d. holes 130 are drilled into the back half of the tip holder 118 and connect into a single coaxial channel 132 which surrounds the ESI source at the front half of the tip holder. These passages serve to direct approximately one half of the gas delivered by the six Teflon® tubes 128 forward through the tip holder and over the ESI tip. The rest of the gas flows backward through channel 115 within the probe body 114 in the spaces between the tubes 126, 128. An additional electrode of 0.5 cm long 11 gauge (2.4 mm i.d., 3.2 mm o.d.) SS tubing 134, is mounted over the ESI tip and in the central channel 132 of the tip holder. It directs the coaxialgas flow 136 over the tip and is held at the ESI potential by a second clip-type spring connector (not shown) touching tube 134.

Figures 10, 11:
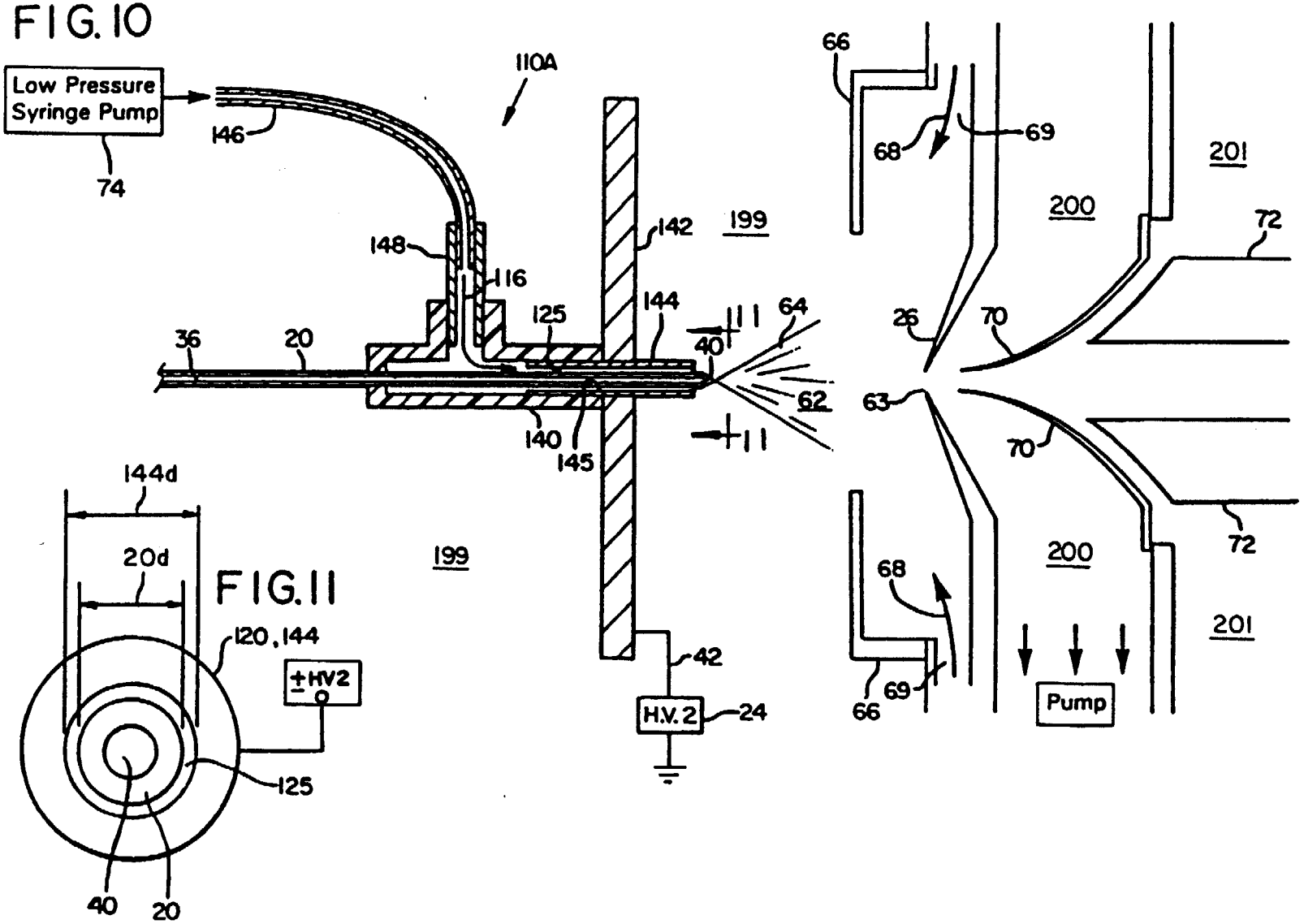
FIG. 10 is a longitudinal cross-sectional view of a first alternate embodiment of a CZE-electrospray-mass-spectrometer interface in accordance with the invention.
FIG. 11 is a transverse cross-sectional view taken along lines 11—11 in FIG. 10.

A second alternative embodiment 110A is shown in FIGS. 10 and 11. The capillary 20 passes through a Lucite® plastic tee 140 mounted on a copper plate 142. A short stainless steel tube 144 having an inside diameter 144d of 0.300 mm passes through plate 142 and inside one leg of tee 140 concentrically to surround the capillary outlet end portion. The steel tube 144 is sized relative to capillary 20 having an outside diameter 20d of 0.250 mm so as to provide an annular passage 145 for the flow of sheath fluid 116 at 1–10 microliters/min around the capillary outlet 40. Such flow is introduced via a second fused silica capillary 146 connected to the remaining leg of the tee by a short copper tube 148. The steel and copper tubes, the copper plate and the buffer liquid introduced via the second capillary are maintained at the ESI voltage.

EXAMPLE 2: RESULTS AND DISCUSSION

ESI Interface Operation

The key improvement provided by the interface shown in FIGS. 10–13 is a much broader range of CZE operating conditions which may be adapted to mass spectrometric detection. For example, the interface allows operation at CZE flow rates previously too small for stable ESI performance (<0.5 uL/min). An ideal electrospray emanates from the fused silica capillary 20 when the electrical contact is made via the conducting liquid 116. In such a mode of operation, ion production is stable and large liquid droplets are not produced as when a nebulizing gas is used. A similar electrospray can also be produced at higher flow rates from a metal capillary, or using the metal-coated fused silica capillaries described previously for CZE-MS (see FIG. 7). At lower flow rates, however, the electrospray enters an unstable mode in which much larger droplets and liquid streams are sporadically produced. Such unstable operation is also characterized by an electrospray emanating from various sites on the metal surface, or moving from one site to another, and resulting in large variations in measured ion currents. Metal surfaces also appear to make a corona discharge more likely, which generally causes loss of analyte signal. Where there are no metal surfaces, the electrospray 64 emanates from the apex of a small liquid cone 138 (FIG. 13), having a volume generally in the range of 5 to 10 nL. This type of electrospray was considered the ideal situation, which we have successfully duplicated with the new interface.

FIG. 13 shows a detailed diagram of the capillary terminus (see also FIG. 11 for end view). The low voltage end 40 of the CZE capillary 20, towards which buffer flows due to electroosmosis, shares the electrical contact with that necessary for electrospray ionization. The voltage at the stainless steel capillary 120 (+3 to 6 kv for positive ion production) thus defines the CZE and ESI field gradients. The actual CZE electrical contact is effectively made with the thin sheath of liquid 116 which flows over the fused silica capillary. The CZE capillary 20 need extend axially only a short distance beyond the metal capillary 120 (>0.2 mm) to provide good performance. The voltage drop across the sheath electrode appears smaller than predicted on the basis of bulk conductivity of the sheath liquid 116 and, under typical conditions, both ESI and CZE performance are consistent with the expected electric field gradients. Thus, the CZE effluent avoids contact with any metal surfaces and is isolated from loss by electrochemical reactions. Interestingly, if the CZE capillary is retracted into the stainless steel capillary, analyte signals are lost even though a visibly unperturbed electrospray is still produced. Presumably, analyte ions are lost due to an electrochemical process at the stainless steel capillary.

The sheath electrode liquid 116 can be the same as the CZE buffer, but it is often advantageous to use another liquid to improve electrospray performance. Since aqueous buffers could not be electrosprayed, our initial studies with CZE-MS used methanol/water buffers (50/50, V%/V%) with a small amount of added electrolyte (e.g., kI). By using either methanol or propanol as the sheath electrode liquid, However, aqueous CZE buffers can be used having up to 0.05M ionic strength. Similarly, the previous limit of $\lesssim$0.01M ionic strength in methanol/water buffers can be circumvented. Typical sheath electrode flow rates are 5 to 10 uL/min, but the range of 2 to 30 uL/min is practical. Since typical CZE flow rates for 100 um i.d. capillaries are in the range of 0.2 to 0.5 uL/min, we anticipate that even greater ionic strength buffers (about 0.1M) can be addressed with smaller diameter capillaries due to the large effective dilution by the sheath liquid. At higher CZE currents (>50 uA), addition of a small amount of electrolyte to the sheath liquid was found to be useful to prevent excessive voltage drop and heating, and a resulting disruption of the electrical contact. Although methanol and isopropanol are not highly conductive liquids, their conductivity appears sufficient given the short distance from the stainless steel capillary to the site of electrospray emission (0.3 to 0.4 mm) for normal CZE currents (<30 uA). Analyte signals are relatively insensitive to the flow rate of the sheath electrode liquid.

The sheath electrode liquid can also be used to modify the electrospray process by either manipulation of the liquid phase chemistry related to ion desorption or, potentially, post-column derivatization to yield an analyte providing distinctive mass spectral information or more efficient ionization. Our results indicate mixing in the electrospray cone 138 (FIG. 13) is extensive since ESI performance can be dramatically improved with CZE buffers which could not be otherwise addressed (i.e., aqueous solutions). We have also used the sheath electrode liquid 116 to introduce components into the electrospray (such as ammonium acetate, trifluoroacetic acid, etc.), and such methods offer significant potential for affecting ESI efficiencies.

The present interface essentially removes any CZE buffer composition and flow rate limitations for ESI. The use of smaller diameter capillaries and CZE media having high viscosities, including gels, is now feasible. In addition, other forms of capillary electrophoresis (isotachophoresis and isoelectric focusing), as well as capillary electrokinetic chromatography, should be more readily coupled with mass spectrometry.

ESI Spectra

The CZE-MS interface allows previously intractable CZE buffers to be effectively electrosprayed. FIG. 14 gives ESI mass spectra for a CZE buffer containing 0.05 sodium dodecylsulfate (SDS) in water obtained using isopropanol at about 5 uL/min flow rate as the sheath electrode liquid. The critical micelle concentration (CMC) for this anionic surfactant is about $8\times10^{-4}$M; thus most of the SDS exists as micelles in the CZE buffer. Negative ion spectra were obtained using the additional sheath gas flow of oxygen to scavenge electrons and suppress discharges similar to the approach first described by Fenn and coworkers (Whitehouse, C. M.; Dreyer, R. N.; Yamashita, M.; Fenn, J. B., "Anal. Chem." 1985, 57, 675-679). The negative ESI spectrum shown in FIG. 14A shows only the dodecylsulfate anion at m/z 265. A small amount of singly charged dimer was also observed under some conditions at high SDS concentrations. A similar mass spectrum is obtained for much more dilute $10^{-5}$ solutions. The positive ESI spectrum is shown in FIG. 14B. An intense molecular ion due to sodium attachment, is observed, and sensitivity is similar to the negative ion mode. Other ions in the spectrum can be attributed to the sodium cation and impurities. These results are especially encouraging since it appears possible that capillary electrokinetic chromatography, which requires concentrations of generally nonvolatile surfactants in excess of the CMC (Terabe, S.; Otsuke, K.; Ando, T. "Anal. Chem." 1985, 57, 834-841), can be interfaced with mass spectrometry to provide variations in separation selectivity and extension to neutral compounds.

Figure 15:
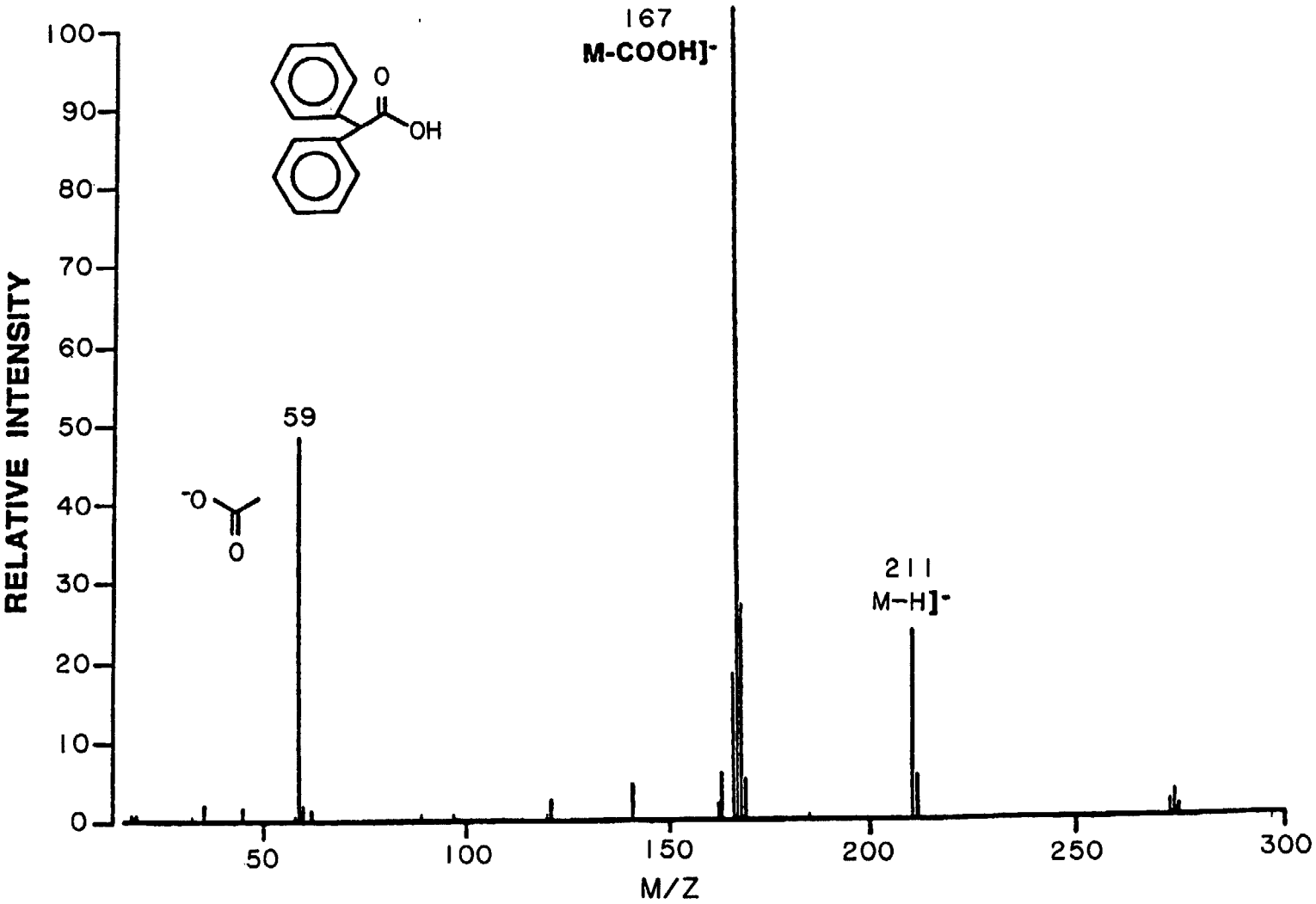
FIG. 15 is an ESI negative ion mass spectrum for diphenylacetic acid.

Two additional observations can be made regarding the ESI mass spectra. First, while fragmentation is generally not observed for the positive ion mode, the negative ion spectra sometimes show useful fragment peaks. For example, the spectrum of diphenylacetic acid (FIG. 15) shows major signals at m/z 59 and 167, as well as the molecular ion (due to H+ loss). Second, the mass spectra shown in FIGS. 14 and 15 are in sharp contrast to those from other desorption ionization methods (i.e., thermospray, particle bombardment, and laser desorption), which give large background signals at m/z<150. This may be related to the relative simplicity of the ESI process compared to other desorption ionization methods, and the fact that the method does not involve either bulk or local heating of the sample.

CZE-MS Separation

The CZE-MS interface using a sheath electrode flow was evaluated using mixtures studied previously of quaternary ammonium salts in water/methanol buffers. Essentially identical performance was obtained yielding $1\text{-}3\times10^5$ theoretical plates and detection limits in the 10 to 100 attomole range. In contrast with our earlier interface, similar separations could also be obtained with aqueous buffers.

Figure 16:
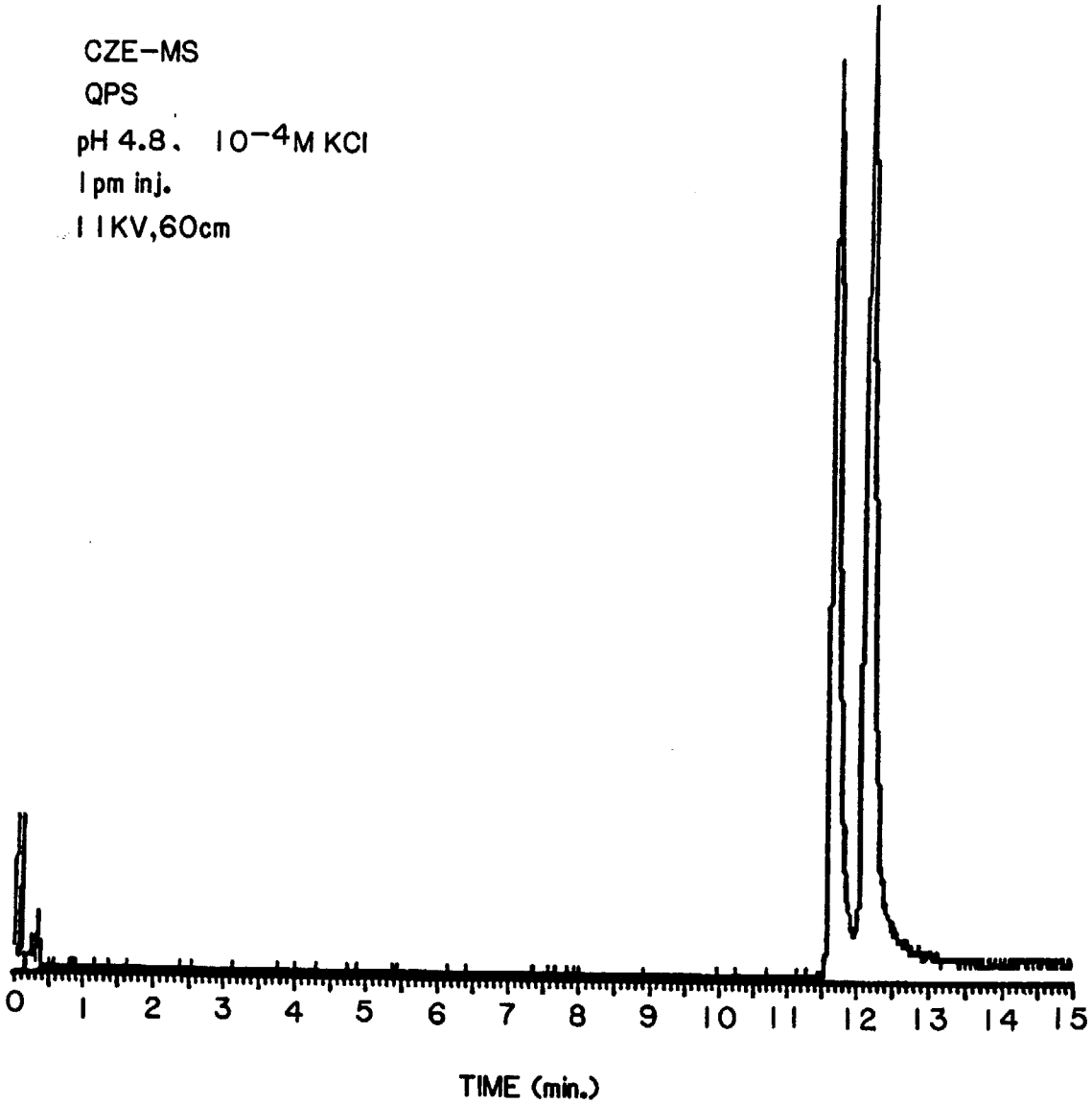
FIG. 16 is a CZE-MS total ion electropherogram for a mixture of quaternary phosphonium salts obtained in a short 60 cm × 100 um i.d. capillary.
Figure 17:
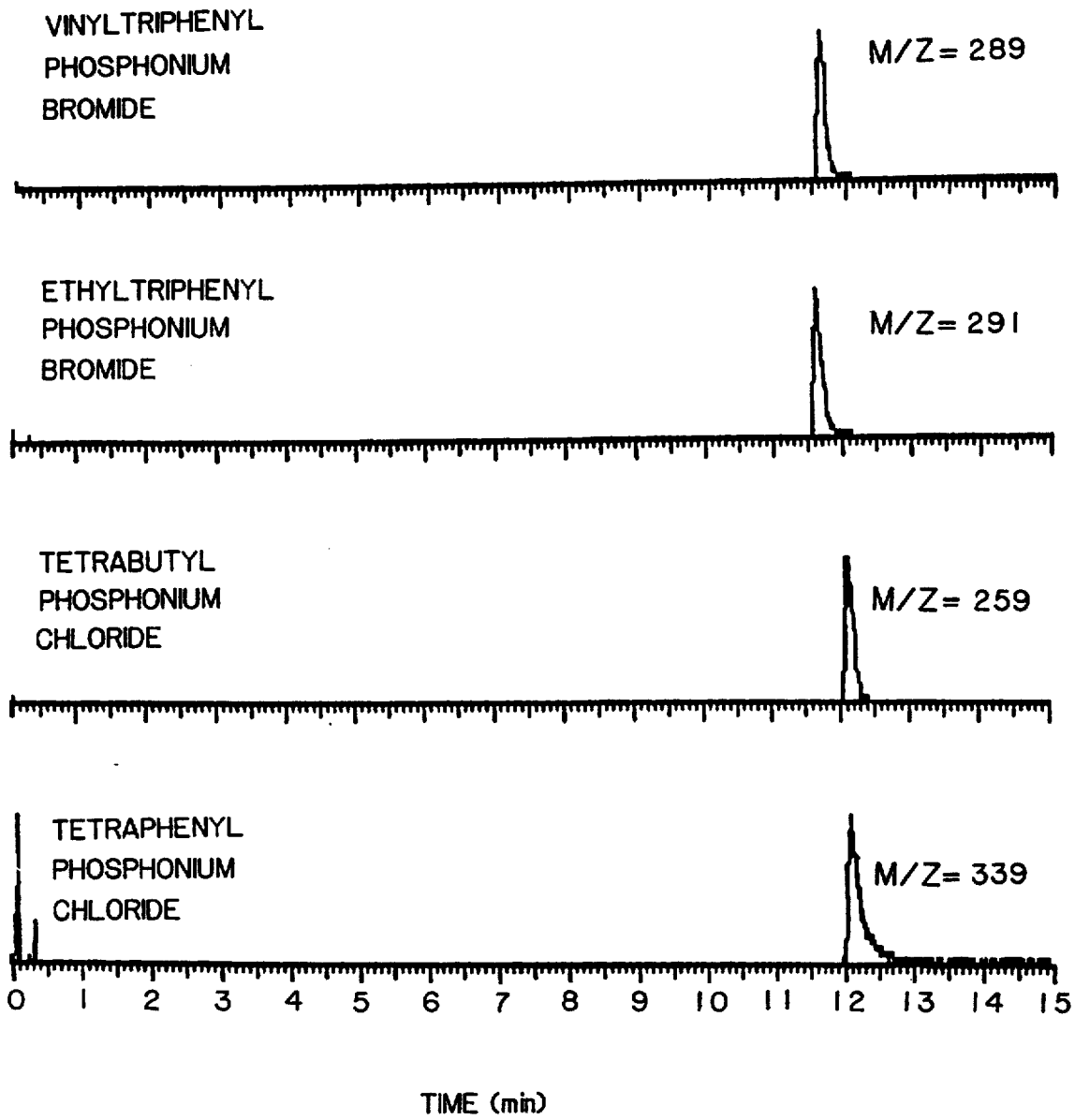
FIG. 17 shows single ion electropherograms for the quaternary phosphonium salts mixture of FIG. 16.

THE CZE-MS total ion electropherogram for a mixture of quaternary phosphonium salts is shown in FIG. 16. Electroosmosis was used to inject a sample plug containing approximately 1 pmole/component, using methods described previously. The separation was conducted in a relatively short 60 cm capillary, using an 11 kV CZE voltage drop. Buffer conductivities were generally chosen to be on the order of $10^3$ umh/cm. The separation in FIG. 16 was obtained using a 0.05M potassium hydrogen phtphale aqueous buffer adjusted ph 4.8 by titration with NaOH and contained a $10^{-3}$M KCl. (It should be noted that inferior separations exhibiting extensive tailing were obtained at higher pH). The sheath electrode liquid was isopropanol containing $10^{-4}$M ammonium acetate. Although 40,000 to 80,000 theoretical plates are obtained in the separation of the individual components, as shown for the single ion electropherograms in FIG. 17, the four component mixture shows only two peaks in FIG. 16. It is not surprising that the vinyltriphenyl and ethyltriphenyl phosphonium ions elute simultaneously due to the expected similarities in their electrophoretic mobilities; it is somewhat less expected that the tetrabutyl and tetraphenyl phosphonium ions also coelute. We anticipate that separations obtained using smaller i.d. or longer capillaries or with alternative buffer systems would provide improved electrophoretic resolution of these components.

Figure 18:
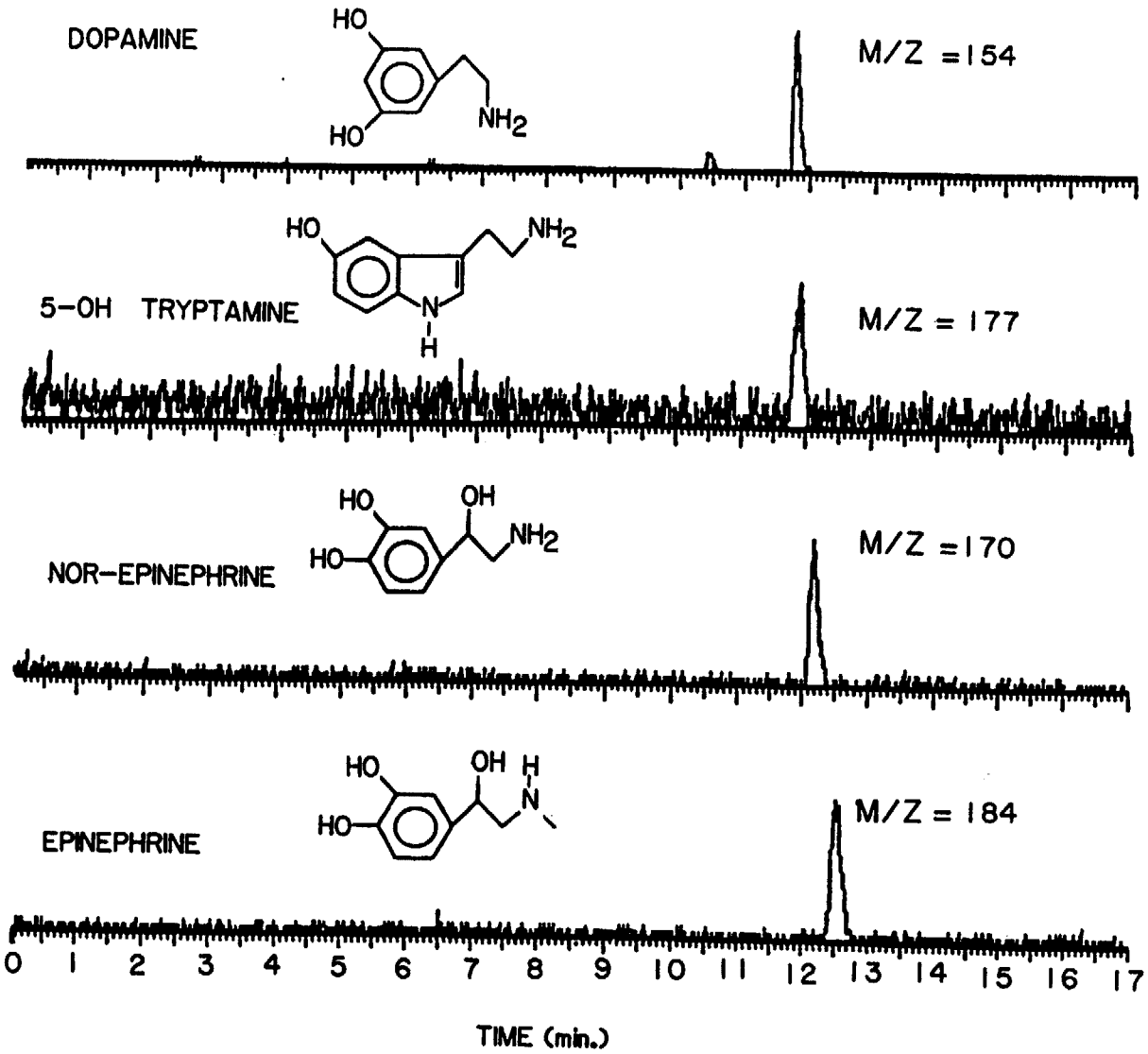
FIG. 18 shows single ion electropherograms for a mixture of amines separated in a short 60 cm × 100 um i.d. capillary.

The single ion electropherograms for a four component mixture of sympathomimetic and relate amines are shown in FIG. 18. In each case, the protonated molecular ion dominated to mass spectrum. The separation was obtained with an 11 kV CZE voltage in a 60 cm×100 um i.d. capillary using a buffer similar to that above adjusted to ph 3.8 with HC1 and containing $10^{-4}$M KCl. Although dopamine and 5-hydroxytrypamine are not electrophoretically resolved, the norepinephrine and epinephine are separated from the other components. Although no attempt has been made to optimize the CZE separations, such results are particularly encouraging due to the biological significance of these compounds.

The CZE-MS interface described here provides the basis for much broader application. The liquid sheath electrode allows the electrospray ionization interface to be operated for almost any buffer system of interest for CZE. This includes aqueous and high ionic strength buffers which could not otherwise be electrosprayed. In addition, the interface provides simplicity of operation and day to day reproducibility not obtained previously. The CZE capillary can be easily and rapidly replaced and no special treatment of preparation is required. The electrospray interface does not affect CZE efficiency and avoids a pressure drop across the capillary, problems which may make other approaches problematic. The sheath flow also provides a convenient method to introduce reagents for mass spectrometer calibration, manipulation of the ESI process, or post-column derivatization. If higher sheath flow rates are desired, a nebulizing gas can be introduced to assist the electrospray process (Bruins, A. P.; Covey, T. R.; Henion, J. D., "Anal. Chem." 1987, 59, 2642–2646).

The CZE-MS approach offers a combination of separation efficiencies and detection limits making it uniquely suited for many biological samples. For example, it is possible to directly couple a micropipette to CZE, providing a basis for direct sampling of single cells and a rapid mass spectrometric characterization of cell contents. A range of both organic and inorganic analysis conventionally addressed by even LC-MS, ion chromatography, and ICP-MS may benefit from CZE-MS when higher resolution separations are required. Separations requiring less than a few minutes are possible by using short capillaries, particularly where sensitive detection methods allow the sample volume to be minimized. Other variations of capillary electrophoresis, including isoelectric focusing, capillary electrokinetic chromatography and isotachophoresis (Everaerts, F. M.; Beckers, J. L.; Verheggen, Th. P. E. M. "Isotachophoresis," J. Chromatogr. Library, Vol 6, Elsevier Science Publishers, Amsterdam, 1976), are amenable to mass spectrometric detection using the new interface.

Figure 19:
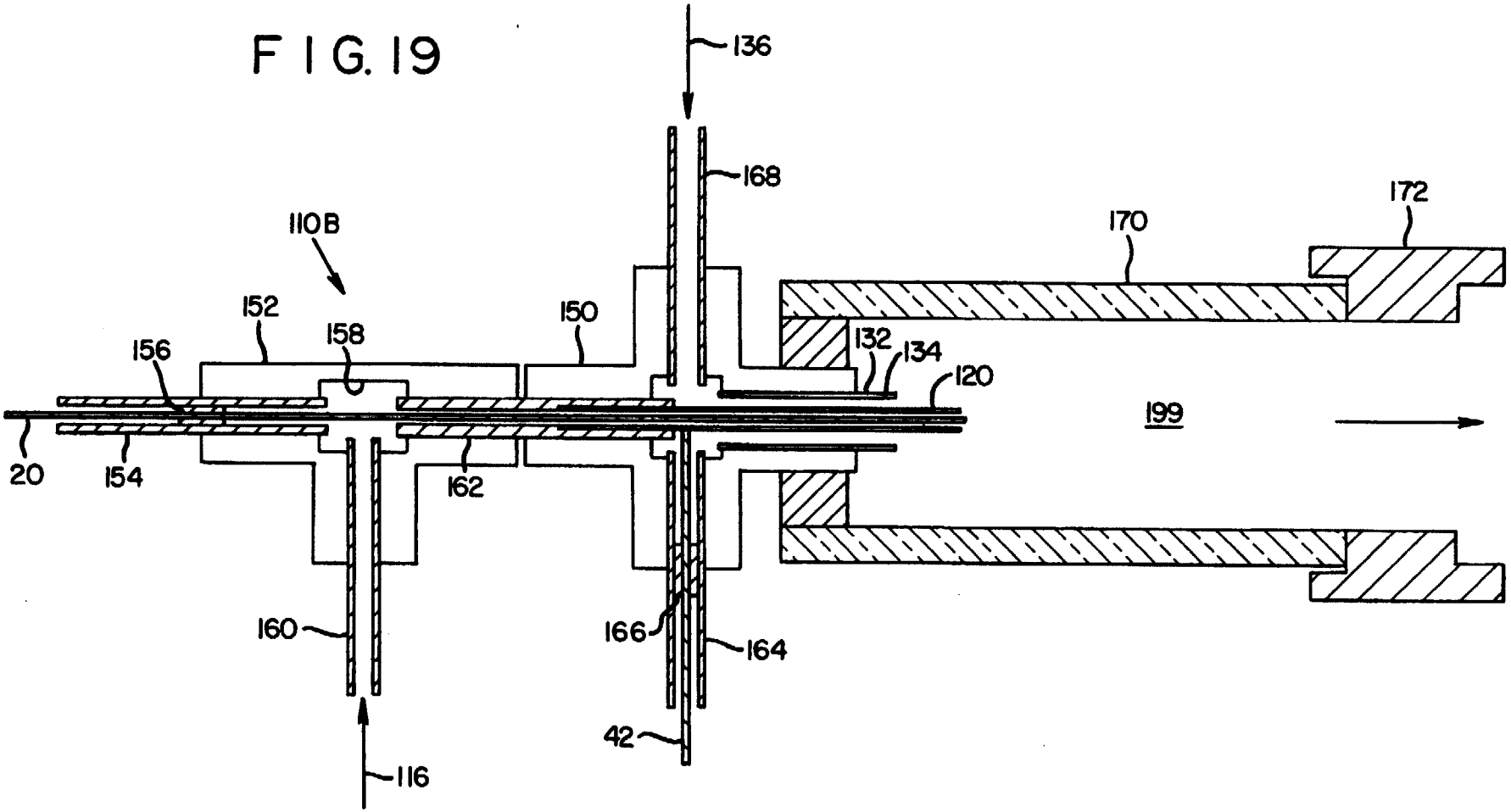
FIG. 19 is a cross-sectional view of a third alternative embodiment of CZE-electrospray interface, adapted for interfacing to a plasma system.

The sheath flow electrospray interface also makes it possible to interface to other forms of analysis. FIG. 19 shows a third alternative embodiment 110B adapted for CZE-electrospray interfacing to plasmas, e.g., for elemental emission, atomic absorption or other known forms of spectroscopy. This interface uses two Teflon® fittings 150, 152. Capillary 20 enters T-fitting 152 through a Teflon® tube 154 and plug 156 and exits through opposed tube 162. Sheath liquid is introduced to T-fitting 152 via tube 160 and flows outside the capillary 20 through tube 162 into a stainless steel tube 120 surrounding capillary 20 in four-way fitting 150. The ESI voltage conductor 42 enters fitting 150 via Teflon® tube 164 and plug 166, and connects to steel tube 120. Sheath gas 136 is introduced to fitting 150 via Teflon® tube 168 and flows outside steel tube 120 toward capillary exit 140. The fourth leg of fitting 150, containing concentric outlets for the CZE eluent, sheath electrode liquid flow and sheath gas flow, is connected to an inlet end of a cylindrical glass spray chamber 170. Spaced axially from these outlets, spray chamber 170 has a stainless steel collar 172 which connects the entire interface to plasma analytic apparatus (not shown) and which is connected into the second high voltage circuit 16B to serve as the electrospray target. Operation of interface 110B is generally as described above for embodiments 110 and 110A. The main difference is the lack of a countercurrent flow to desolvate the electrospray droplets. Also, the sheath gas, typically helium or argon, is necessary to help sustain a plasma. This sheath gas flow is also larger than the auxiliary flows mentioned above, e.g., 0.1 to 2 L/min.

Having illustrated and described the principles of our invention in a preferred embodiment thereof, it should be readily apparent to those skilled in the art that the invention can be modified in arrangement and detail without departing from such principles. The extension of CZE, electrokinetic chromatography or isotachophoresis interfaced using the described electrospray process to other analytical or detection devices as well as off-line sample collection is also part of this invention. Modifications of the electrospray process which involve additional liquid or gas streams, or additional provisions for heating or focusing of the electrospray are also part of this invention. We claim all modifications coming within the spirit and scope of the accompanying claims.

We claim:

1. A method of producing high resolution analyte separations capable of being analyzed by numerous analytical detectors, which comprises:

providing a source of an analyte sample solution and a source of a sheath electrode liquid;

electrophoretically separating said analyte sample solution to form a high resolution analyte eluent;

discharging the separated analyte eluent and the sheath electrode liquid in adjoining flows;

electrospraying an electrically-charged spray containing the separated analyte eluent and the sheath electrode liquid.

2. A method according to claim 1 in which the sheath electrode liquid is discharged in a sheath flow surrounding the flow of separated analyte eluent.

3. A method according to claim 2, which includes conducting said electrophoretic separation of the sample solution in an electrically nonconductive capillary, providing a conductive means for electrically contacting the sheath electrode liquid, and coupling said conductive means in a high voltage circuit for electrophoretically separating sample solution and electrospraying the separated analyte eluent and sheath electrode liquid.

4. A method according to claim 1 which includes conducting said electrophoretic separation of the sample solution in a capillary, discharging the separated analyte eluent from a central exit opening in the capillary, and separately discharging the sheath electrode liquid in an annular, sheath flow about the exit of the capillary.

5. A method according to claim 4 which includes applying a high voltage potential to the analyte sample solution between the source of the analyte sample solution and to the sheath electrode liquid to drive said electrophoretic separation.

6. A method according to claim 4 which includes applying a voltage potential between the sheath electrode liquid and a detector or collector spaced in axial proximity to capillary exit opening for electrospraying the separated analyte eluent together with the sheath electrode liquid.

7. A method according to claim 1 including controlling one of sheath electrode liquid flow rate and composition so that the combined flows of analyte eluent and sheath electrode liquid can be electrosprayed.

8. A method according to claim 1 in which the sheath electrode liquid has an ionic strength under $10^{-3}$ molar and a flow rate in a range of 1 to 50 microliters per minute.

9. A method according to claim 1 including independently controlling the electrophoretic separation and electrospraying steps.

10. A system for producing high resolution separation of analyte composition for analysis by an analytical detector, which comprises:

a source of an analyte sample solution;

a source of a sheath electrode liquid;

means for electrophoretically separating said analyte sample solution to form a high resolution analyte eluent;

means for discharging the separated analyte eluent and sheath electrode liquid in adjoining flows; and means for electrospraying said sheath electrode liquid and separated analyte eluent together without substantial distortion of the analyte separation.

11. The system of claim 10, which includes means for directly imparting an electrical potential to said sheath electrode liquid and thereby to the separated analyte eluent immediately prior to said electrospraying.

12. The system of claim 10, which includes an electrically nonconductive capillary for conducting said electrophoretic separation, and means disposed about an outlet end of said capillary for discharging the sheath electrode liquid in an annular sheath flow around the discharged analyte eluent.

13. The system of claim 12, which further includes means for forming an electrical contact with said sheath electrode liquid and thereby with the separated analyte eluent and a first high voltage supply coupled to said electrical contact means to form a first high voltage circuit through said analyte eluent for electrophoretically separating same.

14. The system of claim 12, which further includes means for forming an electrical contact with said sheath electrode liquid and thereby with the separated analyte eluent and a second voltage supply coupled to said electrical contact means to form a second voltage potential between the analyte eluent and a detector or collector in spaced proximity to said outlet end of the capillary for electrospraying the eluent.

15. The system of claim 10, which includes an electrically nonconductive capillary for conducting said electrophoretic separation, said capillary including an outlet section, a conductive tube surrounding said outlet end and spaced outward therefrom to provide a passage surrounding the outlet section, and means for introducing the flow of sheath electrode liquid into the passage, the tube and capillary having axially adjacent outlets positioned to discharge a sheath flow of the sheath electrode liquid around the discharged analyte eluent.

16. The system of claim 15 in which the capillary outlet section protrudes from the outlet of the conductive tube.

17. The system of claim 15, including means for coupling a voltage potential to the conductive tube for electrically contacting said eluting analyte.

18. The system of claim 15, including:

conductive means for making electrical contact with the conductive tube;

detector means for detecting constituents of a spray of the analyte solution;

a first voltage supply means coupled to said conductive means for applying a first high voltage potential between the source and the sheath electrode liquid at the capillary outlet to electrophoretically separate the analyte sample; and a second voltage supply means coupled to said conductive means for applying a second voltage potential between the sheath electrode liquid at the capillary outlet and the detector means.

19. A system for producing high resolution separation of analyte composition for analysis by an analytical detector, which comprises:

a source of an analyte sample solution;

a source of a sheath electode liquid;

means for electrophoretically separating said analyte sample solution to form a high resolution analyte eluent;

means for discharging the separated analyte eluent and sheath electrode liquid in adjoining flows;

means for electrospraying said sheath electrode liquid and separated analyte eluent together without substantial distortion of the analyte separation;

an electrically noncoductive capillary for conducting said electrophoretic separation, said capillary including an outlet section, a conductive tube surrounding said outlet end and spaced outward therefrom to provide a passage surrounding the outlet section; and a tee having the capillary passing through opposite legs thereof and movable axially therein independently of the tube for relatively positioning the outlets of the tube and capillary;

the tube and capillary having axially adjacent outlets positioned to discharge a sheath flow of the sheath electrode liquid around the discharged analyte eluent.

20. The system of claim 10 including means for controlling the flow of sheath electrode liquid independently of the capillary flow.

21. A system according to claim 10 including means for introducing a sheath gas flow surrounding the combined analyte eluent and sheath electrode liquid flows.

*22. A method of producing high resolution analyte separations capable of being analyzed by numerous analytical detectors, which comprises:*

*providing a source of an analyte sample solution and a source of a sheath liquid;*

*separating a source of an analyte sample solution in a capillary to form a flow of analyte eluent;*

*discharging the separated analyte eluent from a central outlet opening in the capillary and separately dis-*

*charging the sheath liquid in a annular sheath flow about the outlet of the capillary in coaxially adjoining flows;*

*electrospraying an electrically-charged spray containing the separated analyte eluent and the sheath liquid; the capillary outlet opening protruding from an outlet of a surrounding sheath flow tube.*

*23. A method of producing high resolution analyte separations capable of being analyzed by numerous analytical detectors, which comprises:*

*providing a source of an analyte sample solution and a source of a sheath liquid;*

*separating said analyte sample solution in a capillary to form a flow of analyte eluent;*

*discharging the separated analyte eluent form a central outlet opening in the capillary and separately discharging the sheath liquid in an annular sheath flow about the outlet of the capillary in coaxially adjoining flows;*

*electrospraying an electrically-charged spray containing the separated analyte eluent and the sheath by applying a voltage potential between the combined flows of analyte eluent and sheath liquid and a detector or collector spaced in axial proximity to capillary outlet opening for electrospraying the separated analyte eluent together with the sheath liquid.*

*24. A method of producing high resolution analyte separations capable of being analyzed by numerous analytical detectors, which comprises:*

*providing a source of an analyte sample solution and a source of a sheath liquid;*

*separating said analyte sample solution to form a flow of analyte eluent;*

*discharging the separated analyte eluent and the sheath liquid in coaxially adjoining flows;*

*electrospraying an electrically-charged spray containing the separated analyte eluent and the sheath liquid, the sheath liquid having an ionic strength under $10^{-3}$ molar and a flow rate in a range of 1 to 50 microliters per minute.*

*25. A method of producing high resolution analyte separations capable of being analyzed by numerous analytical detectors, which comprises:*

*providing a source of an analyte sample solution and a source of a sheath liquid;*

*separating said analyte sample solution to form a flow of analyte eluent by conducting said separation of the sample solution in a nonconductive capillary;*

*discharging the separated analyte eluent from a central outlet opening in the capillary, separately discharging the sheath liquid in an annular sheath flow about the outlet of the capillary, the separated analyte eluent and sheath liquid being discharged in coaxially and adjoining flows;*

*electrospraying an electrically-charged spray containing the separated analyte eluent and the sheath liquid, a voltage potential being applied between the sheath liquid and a detector or collector spaced in axial proximity to the capillary outlet opening for electrospraying the separated analyte eluent together with the sheath liquid.*

*26. A method of introducing an analyte solution to an analytical detector, which comprises:*

*providing a source of an analyte sample solution and a source of sheath liquid:*

*introducing the analyte sample solution to a capillary having an outlet in which the capillary outlet protrudes from an outlet of a surrounding sheath flow tube;*

*discharging the analyte sample solution from the capillary outlet and discharging the sheath liquid in a sheath flow coaxially surrounding the discharged analyte sample solution;*

*electrospraying an electrically-charged spray containing the analyte sample solution and the sheath liquid.*

*27. A method of introducing an analyte solution to an analytical detector, which comprises:*

*providing a source of an analyte sample solution and a source of a sheath liquid;*

*introducing the analyte sample solution to a capillary having an outlet;*

*discharging the analyte sample solution from the capillary outlet and discharging the sheath liquid ina sheath flow coaxially surrounding the discharged analyte sample solution;*

*electrospraying an electrically-charged spray containing the analyte sample solution and the sheath liquid by applying a voltage potential between the combined flows of analyte sample solution and sheath liquid and a detector or collector spaced in axial proximity to the capillary outlet opening for electrospraying the analyte sample solution together with the sheath liquid.*

*28. A method according to claim 27 including controlling one of sheath liquid flow rate and composition so that the combined flows of analyte eluent and sheath liquid can be electrosprayed.*

*29. A method according to claim 27 in which the electrically-charged spray is directed into a mass spectrometer.*

*30. A method introducing an analyte solution to an analytical detector, which comprises:*

*providing a source of an analyte sample solution and a source of a sheath liquid;*

*introducing the analyte sample solution to a capillary having an outlet;*

*discharging the analyte sample solution from the capillary outlet and discharging the sheath liquid in a sheath flow coaxially surrounding the discharged analyte sample solution;*

*electrospraying an electrically-charged spray containing the analyte sample solution and the sheath liquid, the sheath liquid having an ionic strength suitable for electrospraying and a flow rate in a range of 1 to 50 microliters per minute.*

*31. A method of introducing an analyte solution to an analytical detector, which comprises:*

*providing a source of an analyte sample solution and a source of a sheath liquid;*

*introducing the analyte sample solution to a nonconductive capillary having an outlet;*

*discharging the analyte sample solution from the capillary outlet and discharging the sheath liquid in a sheath flow coaxially surrounding the discharged analye sample solution;*

*electrospraying an electrically-charged spray containing the analyte sample solution and the sheath liquid, the sheath liquid being discharged in an annular sheath flow about the outlet of the capillary, and applying a voltage potential between the sheath liquid and a detector or collector spaced in axial proximity to capillary outlet opening for electrospraying the separated analyte eluent together with the sheath liquid.*

*32. A method according to claim 31 including controlling the flow of sheath liquid independently of the analyte sample solution flow.*

*33. A method according to claim 31 including introducing a sheath gas flow surrounding the combined analyte sample solution and sheath liquid flows.*

*34. A method of introducing the analyte solution to an analytical detector, which comprises:*

*providing a source of an analyte sample solution and a source of a sheath liquid;* introducing the analyte sample solution to a capillary having an outlet;

*discharging the analyte sample solution from the capillary outlet and discharging the sheath liquid in a sheath flow coaxially surrounding the discharged analyte sample solution;*

*electrospraying an electrically-charged spray containing the analyte sample solution and the sheath liquid, the sheath flow being discharged from a conductive sheath flow tube surrounding the capillary and the electrospray voltage potential being applied to the sheath flow tube.*

*35. A method of introducing an analyte solution to an analytical detector, which comprises:*

*providing a source of an analyte sample solution and a source of a sheath liquid;*

*introducing the analyte sample solution to a capillary having an outlet;*

*discharging the analyte sample solution from the capillary outlet and discharging the sheath liquid in a sheath flow coaxially surrounding the discharged analyte sample solution;*

*electrospraying an electrically-charged spray containing the analyte sample solution and the sheath liquid, said electrospraying being carried out at near atmospheric pressure.*

*36. A method according to claim 35 including controlling the flow of sheath liquid independently of the analyte eluent flow.*

*37. A method according to claim 35 including introducing a sheath gas flow surrounding the combined analyte eluent and sheath liquid flows.*

*38. A method of introducing an analyte solution to an analytical detector, which comprises:*

*providing a source of an analyte sample solution and a source of a sheath liquid;*

*introducing the analyte sample solution to a capillary having an outlet and*

*discharging the analyte sample solution from the capillary having an outlet and discharging the analyte sample solution from the capillary outlet and discharging the sheath liquid in a sheath flow coaxially surrounding the discharged analyte sample solution;*

*electrospraying an electrically-charged spray containing the analyte sample solution and the sheath liquid, the electrospraying being carried out at near atmospheric pressure and the electrically-charged spray being directed into a differentially-pumped input of a mass spectrometer.*

*39. A method according to claim 38 including controlling one of sheath liquid flow rate and composition so that the combined flows of analyte sample solution and sheath liquid can be electrosprayed.*

*40. A system for introducing an analyte solution to an analytical detector for analysis, which comprises:*

*a source of an analyte sample solution;*

*a source of a sheath liquid;*

*a capillary for conducting the analyte sample solution to a capillary outlet;*

*a sheath flow tube for conducting the sheath liquid to a sheath flow outlet;*

*means for discharging the analyte sample solution and sheath liquid in coaxially adjoining flows;*

*means for electrospraying a combined flow of said sheath liquid and analyte sample solution discharged from the capillary and sheath flow outlets; and*

*means for directly imparting an electrical potential to said sheath liquid and thereby to the discharged analyte sample solution immediately prior to said electrospraying.*

*41. The system of claim 40, in which the sheath flow outlet is disposed about an outlet end portion of said capillary for discharging the sheath electrode liquid in an annular sheath flow around the discharged analyte sample solution.*

*42. The system of claim 40, in which the sheath flow tube surrounds the capillary and is spaced outward therefrom to provide a passage surrounding the capillary, the tube and capillary having coaxially adjacent outlets positioned to discharge a sheath flow of the sheath electrode liquid around the discharged analyte eluent.*

*43. The system of claim 40 including means for controlling the flow of sheath electrode liquid independently of the capillary flow.*

*44. A system according to claim 40 including means for introducing a sheath gas flow surrounding the combined analyte sample solution and sheath electrode liquid flows.*

*45. A system according to claim 40 including a third tube coaxially surrounding the sheath flow tube and capillary.*

*46. A system according to claim 40 in which the electrospraying is carried out at near atmospheric pressure, the analytical detector is a mass spectrometer and the mass spectrometer includes a differentially-pumped input chamber into which the electrically-charged spray is directed.*

*47. A system according to claim 46 in which the mass spectrometer includes means for sampling and focusing ions from the electrically-charged spray into an analysis chamber.*

*48. A system for introducing an analyte solution to an analytical detector for analysis, which comprises:*

*a source of an analyte sample solution;*

*a source of a sheath liquid;*

*an electrically nonconductive capillary for conducting the analyte sample solution to a capillary outlet;*

*a sheath flow tube for conducting the sheath liquid to a sheath flow outlet, the sheath flow outlet being disposed about an outlet end portion of said capillary for discharging the sheath electrode liquid in an annular sheath flow around the discharged analyte sample solution;*

*means for discharging the analyte sample solution and sheath liquid in coaxially adjoining flows;*

*means for electrospraying a combined flow of said sheath liquid and analyte sample solution discharged from the capillary and sheath flow outlets;*

*means for forming an electrical contact with said sheath liquid and thereby with the analyte sample solution; and*

*a first high voltage supply coupled to said electrical contact means to form a first high voltage circuit through said analyte sample solution for electrophoretically separating same.*

*49. A system for introducing an analyte solution to an analyte solution to an analytical detector for analysis, which comprises:*

*a source of an analyte sample solution;*

*a source of a sheath liquid;*

*a capillary for conducting the analyte sample solution to a capillary outlet;*

*a sheath flow tube for conducting the sheath liquid to a sheath flow outlet, the sheath flow outlet being disposed about an outlet end portion of said capillary for discharging the sheath electrode liquid in an annular sheath flow around the discharged analyte sample solution;*

*means for discharging the analyte sample solution and sheath liquid in coaxially adjoining flows;*

*means for electrospraying a combined flow of said sheath liquid and analyte sample solution discharged from the capillary and sheath flow outlets;*

*means for forming an electrical contact with said sheath liquid and analyte sample solution; a second voltage supply coupled to form a second voltage potential between the combined flow of said sheath liquid and analyte sample solution; and*

*a detector or collector in spaced proximity to said outlet of the capillary for electrospraying the eluent.*

*50. A system for introducing an analyte solution to an analytical detector for analysis, which comprises:*

*a source of an analyte sample solution;*

*a source of a sheath liquid;*

*a capillary for conducting the analyte sample solution to a capillary outlet section;*

*a sheath flow tube for conducting the sheath liquid to a sheath flow outlet, the sheath flow tube surrounding the capillary and spaced outward thereform to provide a passage surrounding the capillary, the tube and capillary having coaxially adjacent outlets positioned to discharge a sheath flow of the sheath electrode liquid around the discharged analyte eluent, the capillary outlet section protruding from the outlet of the sheath flow tube;*

*means for discharging the analyte sample solution and liquid in coaxially adjoining flows; and*

*means for electrospraying a combined flow of said sheath liquid and analyte sample solution discharged from the capillary*

*51. A system for introducing an analyte solution to an analytical detector for analysis, which comprises:*

*a source of an analyte sample solution;*

*a source of a sheath liquid;*

*a capillary for conducting the analyte sample solution to a capillary outlet section;*

*a sheath flow tube for conducting the sheath liquid to a sheath flow outlet, the sheath flow tube surrounding the capillary and spaced outward therefrom to provide a passage surrounding the capillary, the tube and capillary having coaxially adjacent outlets positioned to discharge a sheath flow of the sheath electrode liquid around the discharged analyte eluent;*

*means for discharging the analyte sample solution and sheath liquid in coaxially adjoining flows; and*

*means for electrospraying a combined flow of said sheath liquid and analyte sample solution discharged from the capillary and sheath flow outlets including means for coupling a voltage potential to one of the capillary and the sheath flow tube for electrospraying the combined flow of said sheath liquid and analyte sample solution.*

*52. A system for introducing an analyte solution to an analytical detector for analysis, which comprises:*

*a source of an analyte sample solution;*

*a source of a sheath liquid;*

*a capillary for conducting the analyte sample solution to a capillary outlet;*

*a sheath flow tube for conducting the sheath liquid to a sheath flow outlet;*

*means for discharging the analyte sample solution and sheath liquid in coaxially adjoining flows;*

*means for electrospraying a combined flow of said sheath liquid and analyte sample solution discharged from the capillary and sheath flow outlets;*

*the capillary including an outlet section, the sheath flow tube surrounding said outlet section and being spaced outward therefrom to provide a passage surrounding the outlet section; and*

*a tee having the capillary passing through opposite legs thereof and movable axially therein independently of the sheath flow tube for relatively positioning the outlets of the tube and capillary;*

*the tube and capillary having coaxially adjacent outlets positioned to discharge a sheath flow of the sheath electrode liquid around the discharged analyte sample solution.*

*53. A system for introducing an analyte solution to an analytical detector for analysis, which comprises:*

*a source of an analyte sample solution;*

*a source of a sheath liquid;*

*a capillary for conducting the analyte sample solution to a capillary outlet;*

*a sheath flow tube for conducting the sheath liquid to a sheath flow outlet;*

*means for discharging the analyte sample solution and sheath liquid in coaxially adjoining flows;*

*means for electrospraying a combined flow of said sheath liquid and analyte sample solution discharged from the capillary and sheath flow outlets; and*

*a third tube coaxially surrounding the sheath flow tube and capillary the third tube including a plurality of tubes extending along the sheath flow tube and having outlets spaced from the capillary and sheath flow outlets for conducting a sheath a gas to the interior of the third tube such that a first portion of the sheath gas is discharged forwardly along the coaxially adjoining flows and a second portion of the sheath gas is discharged rearwardly along the tubes.*

*54. A system for introducing an analyte solution to an analytical detector for analysis, which comprises:*

*a source of an analyte sample solution;*

*a source of a sheath liquid;*

*a capillary for conducting the analyte sample solution to a capillary outlet;*

*a sheath flow tube for conducting the sheath liquid to a sheath flow outlet;*

*means for discharging the analyte sample solution and sheath liquid in coaxially adjoining flows;*

*means for electrospraying a combined flow of said sheath liquid and analyte sample solution discharged from the capillary and sheath flow outlets; and*

*the electrospraying being carried out at near atmospheric pressure, the analytical detector being a mass spectrometer and the mass spectrometer including a differentially-pumped input chamber into which the electrically-charged spray is directed, the mass spectrometer including means for desolvating the electrically-charged spray.*

* * * * *